United States Patent
Goto et al.

(10) Patent No.: US 11,707,609 B2
(45) Date of Patent: Jul. 25, 2023

(54) BALLOON CATHETER, METHOD OF MANUFACTURING A BALLOON CATHETER, AND TREATMENT METHOD

(71) Applicant: TERUMO KABUSHIKI KAISHA, Tokyo (JP)

(72) Inventors: Hiroshi Goto, Kanagawa (JP); Yu Murata, Kanagawa (JP); Ryosuke Suzuki, Kanagawa (JP); Yasuo Kurosaki, Kanagawa (JP); Katsumi Morimoto, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 397 days.

(21) Appl. No.: 16/137,016

(22) Filed: Sep. 20, 2018

(65) Prior Publication Data
US 2019/0015641 A1     Jan. 17, 2019

Related U.S. Application Data

(63) Continuation of application No. PCT/JP2017/011632, filed on Mar. 23, 2017.

(30) Foreign Application Priority Data

Mar. 23, 2016  (JP) .................. 2016-058031
Mar. 23, 2016  (JP) .................. 2016-058032

(51) Int. Cl.
*A61M 25/10*     (2013.01)
*A61L 29/16*     (2006.01)
(Continued)

(52) U.S. Cl.
CPC ....... *A61M 25/1027* (2013.01); *A61K 31/337* (2013.01); *A61K 31/436* (2013.01);
(Continued)

(58) Field of Classification Search
CPC .......... A61M 25/1002; A61M 25/1004; A61M 25/10; A61M 25/1027; A61M 2025/105;
(Continued)

(56) References Cited

U.S. PATENT DOCUMENTS

2009/0246252 A1 * 10/2009 Arps .................... A61L 29/145
                                                         424/425
2010/0068170 A1    3/2010 Michal et al.
(Continued)

FOREIGN PATENT DOCUMENTS

CN     103260692 A    8/2013
JP     2012502690 A   2/2012
(Continued)

OTHER PUBLICATIONS

International Search Report (PCT/ISA/210) dated Jun. 27, 2017, by the Japanese Patent Office as the International Searching Authority for International Application No. PCT/JP2017/011632.
(Continued)

*Primary Examiner* — Kami A Bosworth
*Assistant Examiner* — Antarius S Daniel
(74) *Attorney, Agent, or Firm* — Buchanan Ingersoll & Rooney PC

(57) ABSTRACT

A balloon catheter is disclosed that can effectively deliver a drug to living body tissue, a method of manufacturing a balloon catheter, and a treatment method. A balloon catheter is disclosed, the balloon catheter is provided on an outer surface of a balloon with a plurality of elongate bodies which are independent crystals of a water-insoluble drug extending in an elongate form. The elongate bodies include fixed-side elongate bodies which are fixed to the outer surface side of the balloon, and top-side elongate bodies
(Continued)

which are bent or broken from the fixed-side elongate bodies and are continuous with or independent of the fixed-side elongate bodies.

20 Claims, 19 Drawing Sheets

(51) Int. Cl.
*A61K 31/337* (2006.01)
*A61K 31/436* (2006.01)

(52) U.S. Cl.
CPC .............. *A61L 29/16* (2013.01); *A61M 25/10* (2013.01); *A61M 25/1002* (2013.01); *A61L 2300/41* (2013.01); *A61L 2300/416* (2013.01); *A61L 2420/06* (2013.01); *A61M 2025/105* (2013.01); *A61M 2025/1075* (2013.01)

(58) Field of Classification Search
CPC .. A61M 2025/1075; A61M 2025/1043; A61M 2025/1086; A61M 2025/1084; A61M 2025/1081; A61L 27/54; A61L 2300/416
See application file for complete search history.

(56) References Cited

U.S. PATENT DOCUMENTS

| | | | |
|---|---|---|---|
| 2013/0303982 A1 | 11/2013 | Morero et al. | |
| 2014/0271775 A1* | 9/2014 | Cleek | A61L 27/56 424/423 |
| 2014/0358122 A1* | 12/2014 | Yamashita | A61M 25/10 604/509 |
| 2016/0008522 A1 | 1/2016 | Yamashita et al. | |
| 2016/0038648 A1* | 2/2016 | Gemborys | A61L 27/54 424/423 |

FOREIGN PATENT DOCUMENTS

| | | |
|---|---|---|
| JP | 2014200312 A | 10/2014 |
| JP | 2015042280 A | 3/2015 |
| WO | 2014163092 A1 | 9/2014 |
| WO | 2014/163092 A1 | 10/2014 |
| WO | 2015/174000 A1 | 11/2015 |

OTHER PUBLICATIONS

Written Opinion (PCT/ISA/237) dated Jun. 27, 2017, by the Japanese Patent Office as the International Searching Authority for International Application No. PCT/JP2017/011632.
English translation of the Written Opinion of the International Searching Authority and Search Report dated Jun. 27, 2017 in International Application No. PCT/JP2017/011632.
The extended European Search Report dated Jul. 4, 2019, by the European Patent Office in corresponding European Patent Application No. 17770319.6-1132. (5 pages).
Office Action (The First Office Action) dated Sep. 15, 2020, by the State Intellectual Property Office of People's Republic of China in corresponding Chinese Patent Application No. 201780019570.7 and an English Translation of the Office Action. (21 pages).
Office Action (Notice of Reasons for Refusal) dated Jan. 4, 2021, by the Japanese Patent Office in corresponding Japanese Patent Application No. 2018-507393 and an English Translation of the Office Action. (10 pages).

* cited by examiner

BALLOON CATHETER, METHOD OF MANUFACTURING A BALLOON CATHETER, AND TREATMENT METHOD

CROSS-REFERENCES TO RELATED APPLICATIONS

This application is a continuation of International Application No. PCT/JP2017/011632 filed on Mar. 23, 2017, which claims priority to Japanese Application No. 2016-058031 filed on Mar. 23, 2016, and Japanese Application No. 2016-058032 filed on Mar. 23, 2016, the entire contents of all three of which is incorporated herein by reference.

TECHNICAL FIELD

The present disclosure generally relates to a balloon catheter provided with a crystalline drug on a surface of a balloon and a method of manufacturing a balloon catheter, and a method of treatment in which the balloon catheter is used.

BACKGROUND DISCUSSION

In recent years, balloon catheters have been used for improving lesion affected areas (stenosed parts) in body lumens. A balloon catheter normally includes an elongated shaft portion and a balloon which is provided on the distal side of the shaft portion and is inflatable in the radial direction. After the balloon in a deflated state is brought to a target site in the body by way of a thin body lumen, the balloon is inflated, whereby the lesion affected area can be pushed wide open (i.e., widened).

If a lesion affected area is forcibly pushed open, however, excessive proliferation of smooth muscle cells may occur, causing new stenosis (restenosis) at the lesion affected area. In view of this, recently, drug eluting balloons (DEBs) wherein an outer surface of a balloon is coated with a drug for restraining stenosis have been used. The drug eluting balloon, by being inflated, is able to instantaneously release the drug contained in the coating on the outer surface of the balloon to the lesion affected area, thereby restraining restenosis.

In recent years, the morphological form of the drug in the coating on the balloon outer surface can influence the releasing property of the drug from the balloon surface and/or the tissue transferability of the drug at the lesion affected area. For example, U.S. Patent Application Publication No. 2014/0271775 describes a balloon catheter wherein crystals of a drug are formed in an elongated form on a surface of a balloon.

SUMMARY

For enhancing a therapeutic effect, a drug eluting balloon catheter is desirably configured in such a manner that the deliverability of the drug on the surface of the balloon to living body tissue is relatively high.

A balloon catheter is disclosed by which a drug can be effectively delivered to living body tissue, a manufacturing method of the balloon catheter, and a method of treatment in which the balloon catheter is used.

A balloon catheter is disclosed, the balloon catheter being provided on an outer surface of a balloon with a plurality of elongate bodies which are crystals of a water-insoluble drug extending while having independent long axes, wherein the elongate bodies include fixed-side elongate bodies which are fixed to an outer surface side of the balloon and top-side elongate bodies which are bent or broken from the fixed-side elongate bodies and are continuous with or independent of the fixed-side elongate bodies.

In accordance with an aspect, the balloon catheter has the fixed-side elongate bodies and the top-side elongate bodies formed through bending or breaking of the elongate bodies which are crystals of a water-insoluble drug; therefore, the density of the crystals of the drug on the outer surface of the balloon is enhanced, and the surface area of the crystals making contact with living body tissue is enlarged. For this reason, releasing property of the drug from the outer surface of the balloon (i.e., ability of the drug to be released from the outer surface) and transferability of the drug to the living body tissue can be enhanced (i.e., the transferability of the drug onto to the tissue), and the drug can be effectively delivered to the living body tissue. Note that an outer surface side of the balloon includes not only the outer surface of the balloon itself but also an outer surface and the inside of a layer (for example, a layer that contains an excipient) formed on the outer surface of the balloon.

The balloon may have an overlapping portion where portions of the outer surface of the balloon overlap with each other when the balloon is folded in a deflated state, and the fixed-side elongate bodies and the top-side elongate bodies may be provided on the portions of the outer surface of the balloon which overlap with each other at the overlapping portion, can help ensure that the fixed-side elongate bodies and the top-side elongate bodies are not exposed to the exterior in the deflated state of the balloon, so that the fixed-side elongate bodies and the top-side elongate bodies can be protected until the balloon reaches a target position. Therefore, the drug can be restrained from falling off (i.e., being removed from) the outer surface of the balloon or flowing away into blood stream during delivery, and the drug can be effectively delivered to the living body tissue.

In accordance with another aspect, the top-side elongate body may be continuous from the fixed-side elongate body, with a bent portion bent from the fixed-side elongate body between the top-side elongate body and the fixed-side elongate body. Since the elongate bodies are bent at the bent portions, the density of the crystals of the drug on the outer surface of the balloon is enhanced, and the surface area of the crystals making contact with the living body tissue can be enlarged. For this reason, the releasing property of the drug from the outer surface of the balloon and the transferability of the drug to the living body tissue can be enhanced, and the drug can be effectively delivered to the living body tissue.

In accordance with an aspect, the top-side elongate bodies may be independent of the fixed-side elongate body, and may not be fixed to the outer surface side of the balloon but may be held between a plurality of the fixed-side elongate bodies, which helps ensure that the density of the crystals of the drug on the outer surface of the balloon is enhanced, and the surface area of the crystals making contact with the living body tissue is enlarged. In addition, end portions of the fixed-side elongate bodies and the top-side elongate bodies are liable (i.e., likely) to pierce the living body tissue, and, further, the top-side elongate bodies can be easily moved to the living body tissue because they are independent from the fixed-side elongate bodies. For this reason, releasing property of the drug from the outer surface of the balloon and transferability of the drug to the living body tissue can be enhanced, and the drug can be effectively delivered to the living body tissue.

The top-side elongate bodies may have end portions in contact with the outer surface of the balloon side. As a result of this, the top-side elongate bodies are favorably held onto the outer surface of the balloon without falling off the outer surface of the balloon, and the top-side elongate bodies can be carried (i.e., moved) in a favorable manner.

The water-insoluble drug may be rapamycin, paclitaxel, docetaxel, or everolimus. As a result of this, restenosis of a stenosed part in a blood vessel can be favorably restrained by the elongate bodies having the bent portions.

In addition, a method of manufacturing a balloon catheter according to the present disclosure is a method of manufacturing a balloon catheter provided on an outer surface of a balloon with a plurality of elongate bodies which are crystals of a water-insoluble drug extending while having independent long axes, the method including the steps of: forming the elongate bodies on the outer surface of the balloon; forming the balloon with a wing portion projecting in a radial direction; and folding along a circumferential direction the wing portion formed in the balloon, wherein in at least one of the wing portion forming step and the wing portion folding step, the elongate bodies are bent or broken by a force exerted for deforming the balloon, such as to form fixed-side elongate bodies that are fixed to an outer surface side of the balloon and top-side elongate bodies that are bent or broken from the fixed-side elongate bodies and are continuous with or independent of the fixed-side elongate bodies. According to the method of manufacturing a balloon catheter configured as above-mentioned, the fixed-side elongate bodies and the top-side elongate bodies can be efficiently formed by utilizing the force exerted on the balloon in the step of forming the balloon with the wing portion or in the step of folding the wing portion.

In accordance with an aspect, in the wing portion folding step, an overlapping portion where portions of the outer surface of the balloon overlap with each other may be formed, and the elongate bodies provided on the outer surface located at the overlapping portion may be bent or broken to form the fixed-side elongate bodies and the top-side elongate bodies. As a result of this, the force exerted on the balloon for folding the wing portion acts indirectly on the surfaces located inside the overlapping portion, and, therefore, the force acting on the elongate bodies can be controlled, and a desirable force for folding the elongate bodies can be exerted relatively easily.

In accordance with another aspect, a treatment method according to the present disclosure is a treatment method of delivering a drug to a lesion affected area in a body lumen by use of the aforementioned balloon catheter, the treatment method including the steps of: inserting the balloon into the body lumen to deliver the balloon to the lesion affected area; inflating the balloon to press the fixed-side elongate bodies and the top-side elongate bodies against living body tissue; and deflecting the balloon and withdrawing the balloon out of the body lumen. According to the treatment method configured as above, the presence of the fixed-side elongate bodies and the top-side elongate bodies can help ensure that the balloon high in the density of crystals on the outer surface of the balloon is pressed against the living body tissue, so that the surface area of the crystals making contact with the living body tissue can be enlarged. For this reason, releasing property of the drug from the outer surface of the balloon and transferability of the drug to the living body tissue can be enhanced, and the drug can be effectively delivered to the living body tissue.

BRIEF DESCRIPTION OF THE DRAWINGS

FIGS. 5A-5C depict schematic diagrams depicting examples of the elongate body composed of the drug crystal on the outer surface of the balloon, wherein FIG. 5A depicts a case where the bending angle θ is less than 90 degrees, FIG. 5B depicts a case where the bending angle θ is 90 degrees, and FIG. 5C depicts a case where the bending angle θ exceeds 90 degrees.

FIGS. 18A-18C depict sectional views depicting the balloon folded by a balloon folding apparatus, wherein FIG. 18A depicts a state before folding of the balloon, FIG. 18B depicts a state in which the wing portions are formed by the pleating section, and FIG. 18C depicts a state in which the wing portions are folded by the folding section.

DETAILED DESCRIPTION

Figure 1:
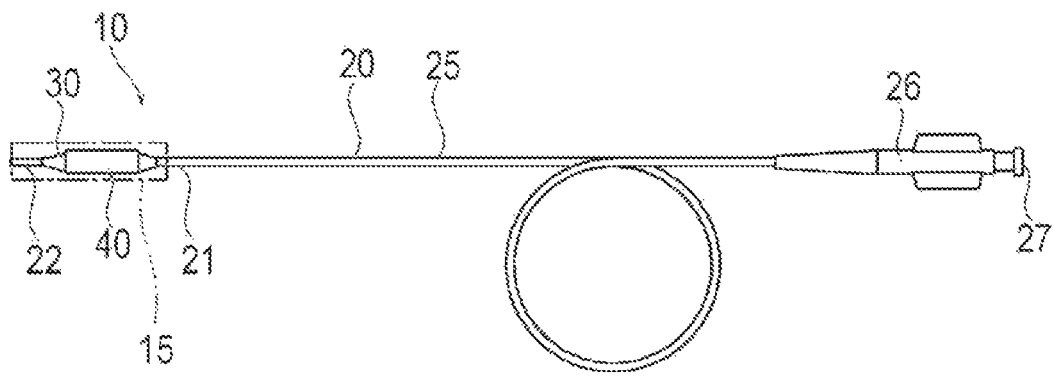
FIG. 1 is a front view of a balloon catheter according to a first embodiment.

Embodiments of the present disclosure will be described below referring to the drawings. Note that for convenience of explanation, the dimensional ratios in the drawings may be exaggerated and different from the actual ratios.

First Embodiment

Figure 2:
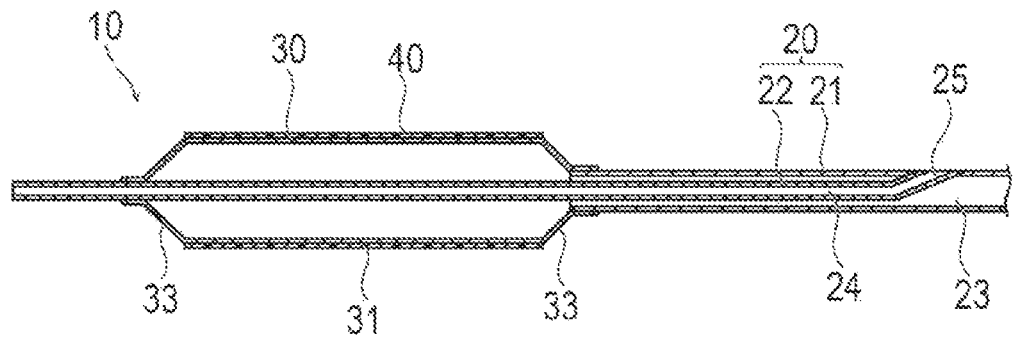
FIG. 2 is a sectional view of a distal portion of the balloon catheter.

As depicted in FIGS. 1 and 2, a balloon catheter 10 according to a first embodiment of the present disclosure is a drug eluting type catheter provided with crystals of a drug on an outer surface of a balloon 30. Note that herein the side on which the balloon catheter 10 is inserted into a body lumen will be referred to as "distal end" or "distal side," while the operator's hand side on which the balloon catheter 10 is operated will be referred to as "proximal end" or "proximal side."

First, the structure of the balloon catheter 10 will be described. The balloon catheter 10 includes an elongated catheter main body 20, the balloon 30 provided on a distal portion of the catheter main body 20, a drug-containing coating layer 40 provided on the outer surface of the balloon 30, and a hub 26 attached to a proximal end of the catheter main body 20. The balloon 30 provided thereon with the coating layer 40 is covered and protected with a protective sheath 15 until put to use.

The catheter main body 20 includes an outer tube 21 which is a tube body opening at distal and proximal ends of the tube body, and an inner tube 22 which is a tube body disposed inside the outer tube 21. The inner tube 22 is accommodated in a hollow (i.e., an annular space or lumen) inside of the outer tube 21, and the catheter main body 20 is of a double tube structure at a distal portion the catheter main body. The hollow inside of the inner tube 22 is a guide wire lumen 24 for passing a guide wire through the guide wire lumen 24. In addition, in the hollow inside of the outer tube 21 and on the outside of the inner tube 22, there is formed an inflation lumen 23 for passing through the inflation lumen 23 an inflation fluid for the balloon 30. The inner tube 22 is open to the exterior at an opening portion 25. The inner tube 22 protrudes to the distal side beyond a distal end of the outer tube 21.

Of the balloon 30, a proximal-side end portion is fixed to a distal portion of the outer tube 21, and a distal-side end portion is fixed to a distal portion of the inner tube 22. It follows that the inside of the balloon 30 communicates with the inflation lumen 23. With the inflation fluid injected through the inflation lumen 23 into the balloon 30, the balloon 30 can be inflated. The inflation fluid may be a gas or a liquid; for example, gases such as helium gas, $CO_2$ gas, $O_2$ gas, $N_2$ gas, Ar gas, air, mixed gas, etc. and liquids such as saline, a contrast agent, etc. can be used as the inflation fluid.

At a central portion in regard of the axial direction of the balloon 30, a hollow cylindrical straight portion 31 (inflatable portion) is formed having an equal outside diameter when inflated. Tapered portions 33 where the outside diameter gradually varies are formed on both sides of the straight portion 31 in regard of the axial direction. In addition, a coating layer 40 which contains a drug is formed on the whole part of an outer surface of the straight portion 31. Note that the range of the balloon 30 in which the coating layer 40 is formed is not limited only to the straight portion 31; the range may include at least part of the tapered portions 33 in addition to the straight portion 31, or may be only part of the straight portion 31.

The hub 26 is formed with a proximal opening portion 27 that communicates with the inflation lumen 23 of the outer tube 21 and functions as a port through which the inflation fluid flows in and out.

The length in the axial direction of the balloon 30 is not particularly limited, and is, for example, preferably 5 mm to 500 mm, more preferably 10 mm to 300 mm, and still more preferably 20 mm to 200 mm.

The outside diameter of the balloon 30 when inflated is not particularly limited, and is, for example, preferably 1 mm to 10 mm, and more preferably 2 mm to 8 mm.

An outer surface of the balloon 30 before the formation of the coating layer 40 is smooth and non-porous. The outer surface of the balloon 30 before the formation of the coating layer 40 may be provided with minute holes (i.e., extremely small holes) that do not pierce through the film of the balloon 30. Alternatively, the outer surface of the balloon 30 before the formation of the coating layer 40 may have both a range of being smooth and non-porous and a range of having minute holes that do not pierce through the film of the balloon 30. The minute holes may be sized to have, for example, a diameter of 0.1 µm to 5 µm and a depth of 0.1 µm to 10 µm, and one or more holes may be provided per crystal. Alternatively, the minute holes may be sized to have, for example, a diameter of 5 µm to 500 µm and a depth of 0.1 µm to 50 µm, and one or more crystals may be provided per hole.

Preferably, the balloon 30 has a certain degree of flexibility and a certain degree of hardness such that the drug can be released from the coating layer 40 provided on the surface of the balloon 30 when the balloon 30 is inflated upon arrival at a blood vessel or tissue. Specifically, the balloon 30 is formed from metal or resin. It is preferable that at least the outer surface of the balloon 30 on which to provide the coating layer 40 is formed of resin. Examples of the material which can be used for forming at least the outer surface of the balloon 30 include thermoplastic resins such as polyolefins (e.g., polyethylene, polypropylene, polybutene, ethylene-propylene copolymers, ethylene-vinyl acetate copolymers, ionomers, or mixtures of two or more of the polyolefins), flexible polyvinyl chloride resin, polyamides, polyamide elastomers, nylon elastomers, polyester, polyester elastomers, polyurethane, fluororesins, etc., silicone rubbers, and latex rubbers. Among the materials which can be used for forming at least the outer surface of the balloon 30, preferred are the polyamides. Specifically, at least part of the outer surface of the balloon 30 to be coated with the drug is made of a polyamide. The polyamide is not particularly limited so long as it is a polymer which has an amide linkage. Examples of the polyamide include homopolymers such as polytetramethylene adipamide (nylon 46), polycaprolactam (nylon 6), polyhexamethylene adipamide (nylon 66), polyhexamethylene sebacamide (nylon 610), polyhexamethylene dodecamide (nylon 612), polyundecanolactam (nylon 11), polydodecanolactam (nylon 12), etc., copolymers such as caprolactam/lauryllactam copolymer (nylon 6/12), caprolactam/aminoundecanoic acid copolymer (nylon 6/11), caprolactam/w-aminononanoic acid copolymer (nylon 6/9), caprolactam/hexamethylenediammonium adipate copolymer (nylon 6/66), etc., and aromatic polyamides such as copolymers of adipic acid with metaxylenediamine, or copolymers of hexamethylenediamine with m,p-phthalic acid. Further, polyamide elastomers wherein nylon 6, nylon 66, nylon 11, nylon 12 or the like constitutes hard segments and a polyalkylene glycol, a polyether, an aliphatic polyester or the like constitutes soft segments can also be used as a material of the balloon 30. The aforesaid polyamides may be used either singly or in combination of two or more of them. In particular, the balloon 30 preferably has a smooth surface made from polyamide.

Figure 3:
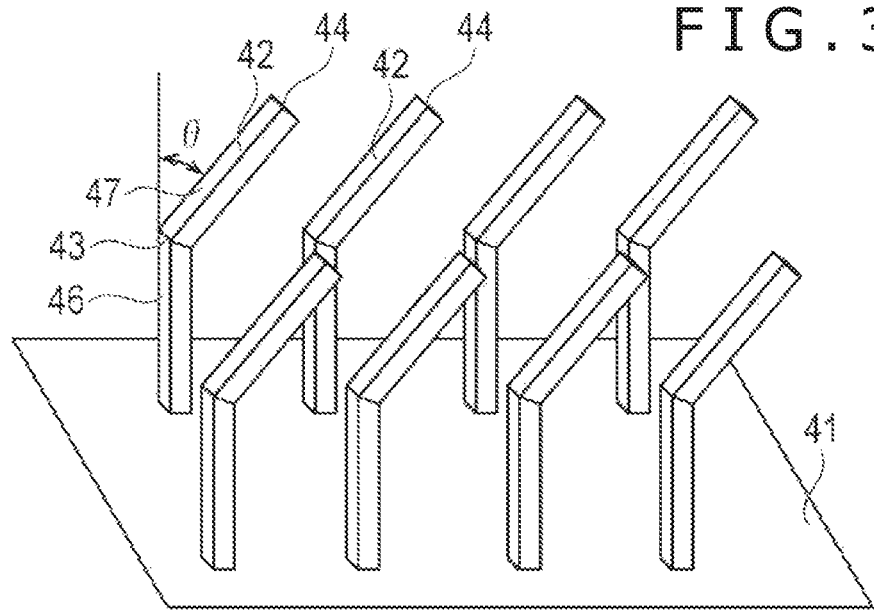
FIG. 3 is a schematic perspective view of elongate bodies composed of drug crystals on an outer surface of a balloon.
Figure 4:
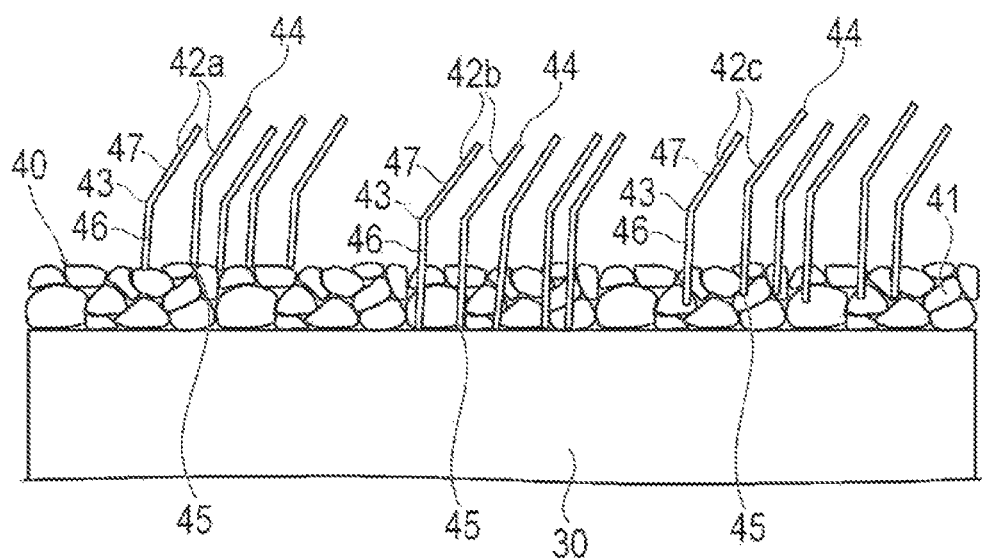
FIG. 4 is a schematic view of the elongate bodies composed of drug crystals and a base material on the outer surface of the balloon.

The balloon 30 is formed on an outer surface of the balloon 20 with a coating layer 40, either directly or through a pre-treatment layer such as a primer layer between the outer surface of the balloon 20 and the coating layer 40, by a method which will be described later. As depicted in FIGS. 3 and 4, the coating layer 40 includes a base material 41 (excipient) which is an additive layer containing a water-soluble low-molecular compound disposed in a layer form on the outer surface of the balloon 30, and a plurality of elongate bodies 42 which are crystals of a water-insoluble drug extending while having independent long axes (i.e., longitudinal axes). The elongate bodies 42 have bent portions 43 bending on both sides of a rectilinear portion in regard of the extending direction of the elongate bodies 42. Each of the elongate bodies 42 has a fixed-side elongate body 46 fixed to the coating layer 40 side, a top-side elongate body 47 in which a crystal having a long axis (i.e., the elongate bodies 42 each possess longitudinal axis that extend or protrudes towards the surrounding environment from the outer surface of the balloon 30 and/or from the coating layer 40) is bent to have a long axis different from that of the fixed-side elongate body 43, and the bent portion 43 between the fixed-side elongate body 46 and the top-side elongate body 47. The top-side elongate body 47 is physically continuous from the fixed-side elongate body 46 on a crystal basis. The bent portion 43 is physically continuous on a crystal basis, and the elongate body 42 is not separated at the bent portion 43. With the elongate body 42 having the bent portion 43, a distal portion of the elongate body 42 enter between other crystals, whereby the density of the crystals can be enhanced, and the surface area of the crystals making contact with the living body tissue is enlarged. Therefore, the releasing property of the drug from the surface of the balloon 30 and the transferability of the drug to the living body tissue can be enhanced, and the drug can be delivered to the living body tissue more effectively. The elongate bodies 42 include first elongate bodies 42a extending from an outer surface of the base material 41 toward the outside of the surface, second elongate bodies 42b extending from the outer surface of the balloon 30 to the outside of the base material 41 by penetrating the base material 41, and third elongate bodies 42c extending from the inside of the base material 41 to the outside of the base material 41. In accordance with an aspect, a base portion (i.e., proximal-most end) 45 of the elongate body 42 may make direct contact with the outer surface of the balloon 30, or may not make direct contact with the outer surface of the balloon 30 and the base material 41 (excipient) may be present between the base portion 45 and the outer surface of the balloon 30. In accordance with an aspect, a top portion 44 of the elongate body 42 does not make contact with either of the balloon 30 and the base material 41 where the base portion 45 of the elongate body 42 is located. Since the elongate bodies 42a, 42b, and 42c differ in deliverability of the drug to the living body, it is possible, by regulating the positions of the base portions 45 of the crystals of the drug, to arbitrarily control the drug deliverability. Preparation may be made such that almost only the elongate bodies 42b exist on the surface of the balloon 30. Preparation may be made such that almost the elongate bodies 42c exist on the surface of the balloon 30. In addition, preparation may be made such that a plurality of kinds of elongate bodies exists in combination on the surface of the balloon 30. Examples of the combination include a combination of the elongate bodies 42a with the elongate bodies 42b, a combination of the elongate bodies 42b with the elongate bodies 42c, and a combination of the elongate bodies 42c with the elongate bodies 42a. Preparation may be made such that all the elongate bodies 42a, 42b, and 42c exist on the surface of the balloon 30.

The plurality of elongate bodies 42 may be regularly disposed on the outer surface of the balloon 30. Alternatively, the plurality of elongate bodies 42 may be irregularly disposed on the outer surface of the balloon 30. In addition, the elongate bodies 42 having the bent portions 43 may be provided throughout the coating layer 40, or may be provided only in part of the coating layer 40. Note that part of the elongate bodies 42 which are crystals of a water-insoluble drug extending while having independent long axes may not have the bent portion 43.

Figure 5A:
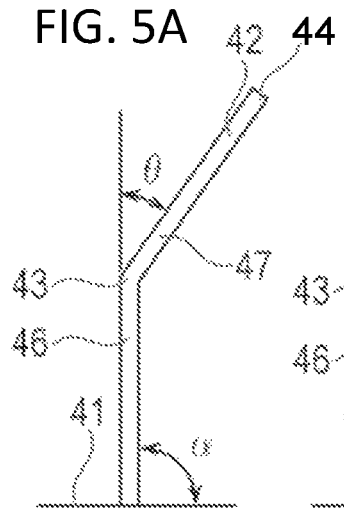
Figure 5B:
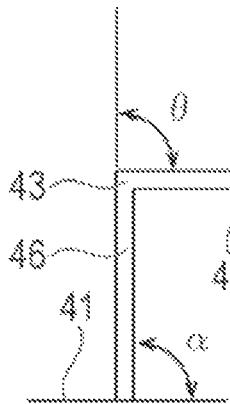
Figure 5C:
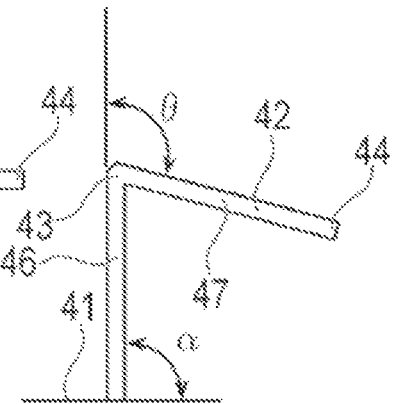

The bending angle θ relative to the extending direction of the elongate body 42, at the bent portion 43 of the elongate body 42 which is a crystal of the drug, is not particularly limited so long as the bending angle θ is more than 0 degrees and less than 180 degrees. Therefore, the bending angle may be less than 90 degrees, for example, as depicted in FIG. 5A, may be 90 degrees, as depicted in FIG. 5B, or may be more than 90 degrees, as depicted in FIG. 5C. The bending angle θ is, for example, preferably 1 to 179 degrees, more preferably 30 to 150 degrees, and still more preferably 45 to 135 degrees. The bending angles θ of the individual elongate bodies 42 may be substantially equal, or may be different from elongate body 42 to elongate body 42. In addition, the directions in which the elongate bodies 42 bend may be regular (i.e., the same direction) or may be irregular (i.e., different directions).

The inclination angle α of the elongate bodies 42 relative to the outer surface of the balloon 30 or the base material 41 is not particularly limited, and the inclination angle α, for example, may be 45 degrees to 135 degrees, preferably 60 degrees to 120 degrees, more preferably 75 degrees to 105 degrees, and still more preferably approximately 90 degrees.

Figure 6:
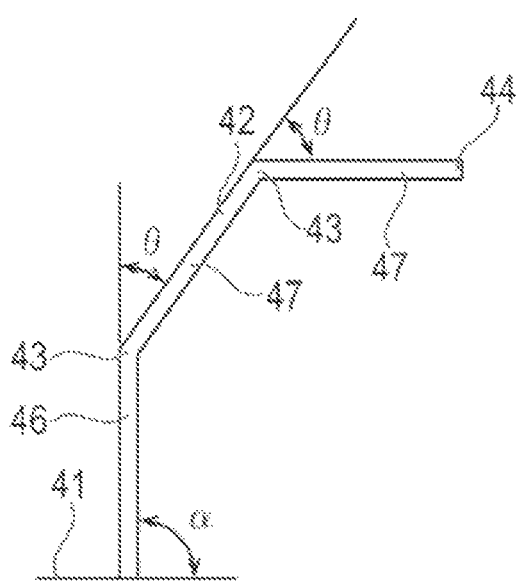
FIG. 6 is a schematic diagram depicting an elongate body having a plurality of bent portions.

As depicted in FIG. 6, the elongate body 42 may have two or more bent portions 43 (in the example depicted in FIG. 6, two bent portions 43). In the case where the elongate body 42 has two bent portions 43, examples of the combination of the bending angle θ of the sturdy portion 43 on the proximal side with the bending angle θ of the sturdy portion 43 on the distal side include a combination wherein the bending angle θ of the sturdy portion 43 on the distal side, for example, is 10 degrees to 89 degrees when the bending angle θ of the sturdy portion 43 on the proximal side is 10 degrees to 90 degrees, and a combination wherein the bending angle θ of the sturdy portion 43 on the distal side is 1 degrees to 34 degrees when the bending angle θ of the sturdy portion 43 on the proximal side is 91 degrees to 135 degrees.

The amount of the drug contained in the coating layer 40 is not particularly limited; for example, the amount in density is 0.1 μg/mm$^2$ to 10 μg/mm$^2$, preferably 0.5 μg/mm$^2$ to 5 μg/mm$^2$, more preferably 0.5 μg/mm$^2$ to 3.5 μg/mm$^2$, and still more preferably 1.0 μg/mm$^2$ to 3 μg/mm$^2$. The amount of the crystals in the coating layer 40 is not particularly limited, and for example, the amount of the crystals in the coating layer 40 is preferably 5 crystals/(10 μm$^2$) to 500,000 crystals/(10 μm$^2$) (the number of crystals per 10 μm$^2$), more preferably 50 crystals/(10 μm$^2$) to 50,000 crystals/(10 μm$^2$), and still more preferably 500 crystals/(10 μm$^2$) to 5,000 crystals/(10 μm$^2$).

The plurality of elongate bodies 42 wherein the crystals have mutually independent long axes may be present in a state where they are combined. The plurality of adjacent elongate bodies 42 may be present in contact with one another while forming different angles between the plurality of adjacent elongate bodies 42. The plurality of elongate bodies 42 may be located with spaces (spaces in which the crystal is not contained) between the plurality of adjacent elongate bodies 42 on the balloon surface. Both a plurality of elongate bodies 42 in a combined state and a plurality of elongate bodies 42 in a separate and independent state may exist on the surface of the balloon 30. The plurality of elongate bodies 42 may be arranged in a circumferential and brush-like pattern while having different long axis directions. The elongate bodies 42 each exist independently, each of the elongate bodies 42 have a certain length, and one end (proximal end) of the length portion of each of the elongate bodies 42 is fixed to the base material 41 or the balloon 30. The elongate body 42 does not form a composite structure, and is not interlocked, with the adjacent elongate bodies 42. The long axes of the crystals are almost rectilinear. The elongate bodies 42 form predetermined angles relative to the surface which their long axes intersect and with which their base portions 45 make contact.

Preferably, the elongate bodies 42 stand (i.e., extend or protrude) independently, without making contact with one another. The base portions 45 of the elongate bodies 42 may be in contact with other base portions 45 on the balloon 30. In addition, the base portions 45 of the elongate bodies 42 may be independent, without making contact with other base portions 45, on the balloon 30.

In accordance with an aspect, the elongate bodies 42 may be hollow or may be solid. Both hollow elongate bodies 42 and solid elongate bodies 42 may exist on the surface of the balloon 30. Where the elongate body 42 is hollow, at least a portion of the elongate body 42 near the tip end of the elongate body 42 is hollow (i.e., contains a space in the interior of the elongate body 42). A section of the elongate body 42 in a plane perpendicular (orthogonal) to the long axis of the elongate body 42 has a void (hollow portion). In the elongate body 42 thus having a void, the section of the elongate body 42 in a plane perpendicular (orthogonal) to the long axis is polygonal in shape. The polygon here is, for example, a triangle, a tetragon, a pentagon, or a hexagon. Therefore, the elongate bodies 42 are each formed as an elongate polyhedron which has a distal end (or a distal surface) and a proximal end (or a proximal surface) and in which a side surface portion between the distal end (or the distal surface) and the proximal end (or the proximal surface) is composed of a plurality of substantially plain surfaces. Alternatively, the elongate bodies 42 may be in a needle shape. This crystalline morphological form (hollow elongate body crystalline morphological form) constitutes the whole part or at least part of a plane, at the surface with which the base portions 45 make contact.

The length in the long axis direction of the elongate bodies 42 having the long axes is, for example, preferably 5 μm to 20 μm, more preferably 9 μm to 11 μm, and still more preferably around 10 μm. Note that the length in the long axis direction of the elongate bodies 42 can be defined by the length before bending at the bent portions 43. The diameter of the elongate bodies 42 having the long axes is, for example, preferably 0.01 μm to 5 μm, more preferably 0.05 μm to 4 μm, and still more preferably 0.1 μm to 3 μm. Examples of the combination of length in the long axis direction and diameter of the elongate bodies 42 having the long axes include a combination of a diameter of, for example, 0.01 μm to 5 μm when the length is 5 μm to 20 μm, a combination of a diameter of 0.05 μm to 4 μm when the length is 5 μm to 20 μm, and a combination of a diameter of 0.1 μm to 3 μm when the length is 5 μm to 20 μm. The elongate bodies 42 having the long axes may be rectilinear in the long axis direction of the elongate bodies 42, and may also be curved in curved line forms. Both rectilinear elongate bodies 42 and curved elongate bodies 42 may exist on the surface of the balloon 30.

The crystalline morphological form including the crystals having the long axes as above-mentioned accounts for at least 50% by volume, more preferably at least 70% by volume, based on the whole of the drug crystals on the outer surface of the balloon 30.

The crystal particles having the long axes after the coating of the coating layer 40 and before the balloon 30 is folded (before the bent portions 43 are formed) are formed not to lie flat but to stand in relation to the outer surface of the balloon 30. In the crystal particles in this instance, the angle of the crystal particle is changed by the pleating (the step of forming the balloon with the wing portions 32) or the folding (the step of folding the wing portions 32) of the balloon 30, whereby the angles of the long axes of the crystal particles relative to the outer surface of the balloon 30 can be changed. Therefore, while the crystals which are formed in the manner of lying flat on the outer surface of the balloon 30 from the beginning are firmly attached (fixed) to the outer surface of the balloon 30 and/or the adjacent crystal particles, the crystal particles which are standing are not formed in the state of being physically fixed to the outer surface of the balloon 30 or the adjacent crystal particles. For this reason, the standing crystal particles are only positioned (arranged) in such a manner as to make contact with, for example, the outer surface of the balloon 30 or the adjacent crystal particles, and the positions of the outer surface of the balloon 30 or the adjacent crystal particles can be changed on a three-dimensional basis. Accordingly, the crystal particles after the coating are formed such that their angles and positions can be changed through the pleating or folding of the balloon 30. Part of the crystal particles may be embedded in the surface of the balloon 30.

The base material 41 is present in the state of being distributed into spaces between the plurality of elongate bodies 42 standing together. The base material 41 may exist in a region where the elongate bodies 42 are present, and may not exist in a region where the elongate bodies 42 are absent. In regard of the proportions of the materials constituting the coating layer 40, the crystals of the water-insoluble drug preferably occupy a larger volume than that occupied by the base material 41. In accordance with an aspect, the excipient constituting the base material 41 does not form a matrix. The matrix is a layer which is configured by continuation of a comparatively high-molecular material (polymer or the like), which forms a network-like three-dimensional structure, and in which minute spaces (i.e., extremely small spaces) are present. Therefore, the water-insoluble drug constituting the crystals is not adhered to the inside of a matrix material. Moreover, the water-insoluble drug constituting the crystals is not embedded in a matrix material.

In accordance with an exemplary embodiment, the base material 41 is formed as a dried layer, after being applied in an aqueous solution state to the outer surface of the balloon 30. The base material 41 is amorphous. The base material 41 may be crystal particles. The base material 41 may exist as a mixture of an amorphous state with crystal particles. The base material 41 in FIG. 4 is in a state including crystal particles and/or particulate amorphous portions. The base material 41 is formed as a layer including the water-insoluble drug. Alternatively, the base material 41 may be formed as an independent layer that does not include the water-insoluble drug. The thickness of the base material 41 is, for example, 0.1 µm to 5 µm, preferably 0.3 µm to 3 µm, and more preferably 0.5 µm to 2 µm.

In accordance with an aspect, the layer including the morphological form of the elongate body crystals is low in toxicity and high in stenosis-inhibiting effect at the time of delivery into a body. The water-insoluble drug including the hollow elongate body crystalline morphological form has good property of penetration into tissue because of a small crystal unit size upon transfer of the drug to the tissue, and, since it has good solubility, it acts effectively and can inhibit stenosis. In addition, it is considered that the drug is less liable to remain in the tissue as large lumps (i.e., in a relatively large lump form) and, therefore, has low toxicity.

In addition, the layer including the elongate body crystalline morphological form has a plurality of substantially uniform elongate bodies 42 having the long axes, and the elongate bodies 42 are substantially uniformly standing together on the surface with which their base portions 45 make contact. Therefore, the size (i.e., the length in the long axis direction) of the crystals transferred to the tissue is as small as, for example, approximately 10 µm. For this reason, the drug uniformly acts on the lesion affected area, with an enhanced property for penetration into the tissue. Furthermore, since the size of the crystals transferred is small, there is no possibility that an excess amount of the drug might remain at the affected area for an excess of time; for this reason, it is considered, the drug can represent a high stenosis inhibitory effect, without depicting toxicity.

The drug in the coating on the outer surface of the balloon 30 may include an amorphous phase. The crystals and the amorphous phase may be disposed regularly in the coating layer 40. Alternatively, the crystals and the amorphous phase may be disposed irregularly.

The protective sheath 15 is a member for inhibiting the drug from falling off the balloon 30, and is removed before the use of the balloon catheter 10. The protective sheath 15 can be formed from a flexible material. Examples of the material which can be used include thermoplastic resins such as polyolefins (e.g., polyethylene, polypropylene, polybutene, ethylene-propylene copolymers, ethylene-vinyl acetate copolymers, ionomers, or mixtures of two or more of the polyolefins), flexible polyvinyl chloride resin, polyamides, polyamide elastomers, polyesters, polyester elastomers, polyurethane, fluororesins, etc., silicone rubbers, and latex rubbers.

The balloon coating system for forming the coating layer 40 on the aforementioned balloon 30 will be described below. The present system includes a balloon coating apparatus 60 (see FIG. 7) for forming the coating layer 40 on the balloon 30, and a balloon folding apparatus 100 (see FIG. 9) for folding the balloon 30 formed with the coating layer 40. By use of the balloon coating apparatus 60, a plurality of elongate bodies 42 which are crystals of a water-insoluble drug extending while having independent long axes are formed on an outer surface of the balloon 30. Thereafter, the balloon 30 is folded by the balloon folding apparatus 100, whereby the plurality of elongate bodies 42 provided on the outer surface of the balloon 30 are deformed in a bending manner.

Figure 7:
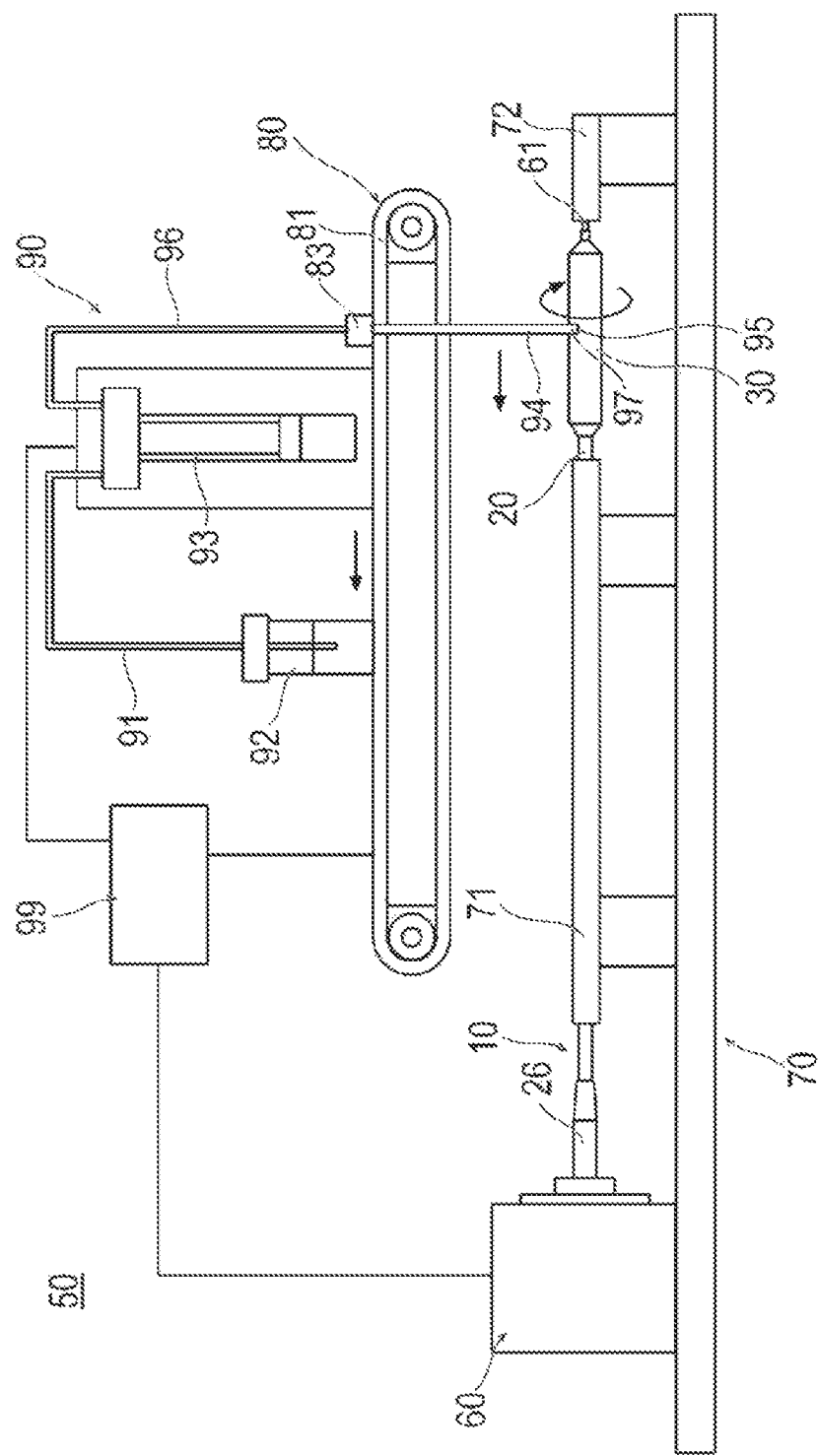
FIG. 7 is a front view of a balloon coating apparatus.
Figure 8:
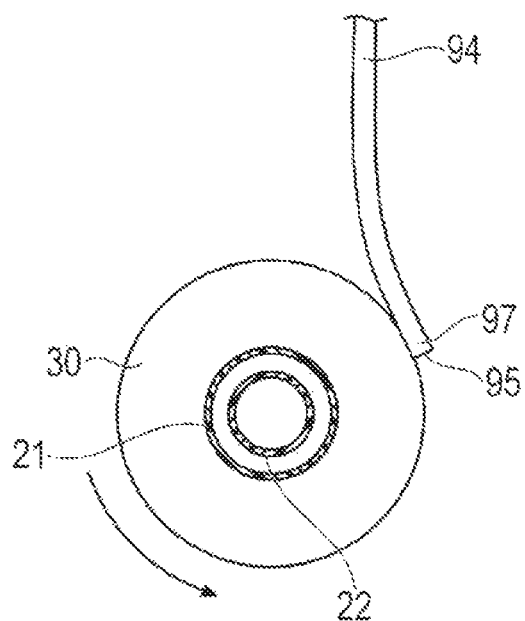
FIG. 8 is a sectional view depicting a dispensing tube in contact with the balloon.

The balloon coating apparatus 60 will be described. As depicted in FIGS. 7 and 8, the balloon coating apparatus 60 includes a rotation mechanism section 61 for rotating the balloon catheter 10, and a support base 70 for supporting the balloon catheter 10. The balloon coating apparatus 60 further includes an application mechanism section 90 provided with a dispensing tube 94 for applying a coating solution to an outer surface of the balloon 30, a movement mechanism section 80 for moving the dispensing tube 94 relative to the balloon 30, and a control unit 99 for controlling the balloon coating apparatus 60.

The rotation mechanism section 60 holds the hub 26 of the balloon catheter 10, and rotates the balloon catheter 10 around an axis of the balloon 30 by a drive source, such as a motor, incorporated in the rotation mechanism 60. The balloon catheter 10 is held, with a core member 62 inserted in the guide wire lumen 24, and the core member 62 helps prevent the coating solution from flowing into the guide wire lumen 24. In addition, for operating the flow of a fluid into the inflation lumen 23, a three-way cock (i.e., a three-way valve) capable of operating the opening/closing of a passage or passages is connected to the proximal opening portion 27 of the hub 26 in the balloon catheter 10.

The support base 70 includes a proximal-side support section 71 that accommodates the catheter main body 20 in the support base 70 and rotatably supports the catheter main body 20, and a distal-side support section 72 that rotatably supports the core member 62. Note that the distal-side support section 72 may, if possible, rotatably support a distal portion of the catheter main body 20, instead of the core member 62.

The movement mechanism section 80 includes a movable base 81 which can be moved rectilinearly in a direction parallel to the axis of the balloon 30, and a tube fixing section 83 to which the dispensing tube 94 is fixed. The movable base 81 can be moved rectilinearly by a drive source, such as a motor, incorporated in the movable base 81. The tube fixing section 83 fixes an upper end of the dispensing tube 94 relative to the movable base 81. With the movable base 81 moved, therefore, the dispensing tube 94 is moved rectilinearly in a direction parallel to the axis of the balloon 30. In addition, the application mechanism section 90 is mounted on the movable base 81, and the movable base 81 moves the application mechanism section 90 rectilinearly in both directions (both senses) along the axis.

The application mechanism section 90 is a section that applies the coating solution to the outer surface of the balloon 30. The application mechanism section 90 includes a container 92 containing the coating solution, a feed pump 93 that feeds the coating solution at an arbitrary feed rate, and the dispensing tube 94 that applies the coating solution to the balloon 30.

The feed pump 93 is, for example, a syringe pump. Controlled by the control unit 99, the feed pump 93 can draw the coating solution from the container 92 through a suction tube 91, and feed the coating solution into the dispensing tube 94 through a supply tube 96 at an arbitrary feed rate. The feed pump 93 is disposed on the movable base 81, and can be moved rectilinearly by the movement of the movable base 81. Note that the feed pump 93 is not limited to the syringe pump so long as it can feed the coating solution, and may be, for example, a tube pump.

The dispensing tube 94 is a member which communicates with the supply tube 96 and discharges to the outer surface of the balloon 30 the coating solution supplied from the feed pump 93 through the supply tube 96. The dispensing tube 94 can be a flexible circular pipe-shaped member. An upper end of the dispensing tube 94 is fixed to the tube fixing section 83, extends downward in the vertical direction from the tube fixing section 83, and is formed with an opening portion 95 at a discharge end 97 which is its lower end. With the movable base 81 moved, the dispensing tube 94 can be moved rectilinearly in both directions (both senses) along the axial direction of the balloon catheter 10, together with the feed pump 93 disposed on the movable base 81. The dispensing tube 94 can supply the coating solution to the outer surface of the balloon 30, in the state of being bent by being pressed against the balloon 30.

Note that the dispensing tube 94 may not necessarily be circular pipe-shaped so long as the dispensing tube 94 can supply the coating solution. In addition, the dispensing tube 94 may not necessarily extend in the vertical direction so long as the dispensing tube 94 can discharge the coating solution through the opening portion 95.

The dispensing tube 94 is preferably formed from a flexible material such that contact burden on the balloon 30 can be reduced and variations in the contact position attendant on the rotation of the balloon 30 can be absorbed by flexure of the dispensing tube 94. Examples of the applicable material for the dispensing tube 94 include polyolefins such as polyethylene, polypropylene, etc., cyclic polyolefins, polyesters, polyamides, polyurethane, and fluororesins such as PTFE (polytetrafluoroethylene), ETFE (tetrafluoroethylene-ethylene copolymer), PFA (tetrafluoroethylene-perfluoroalkyl vinyl ether copolymer), FEP (tetrafluoroethylene-hexafluoropropylene copolymer), etc., but the material is not particularly limited so long as the material of the dispensing tube 94 is flexible and deformable.

The outside diameter of the dispensing tube 94 is not particularly limited, and is, for example, 0.1 mm to 5.0 mm, preferably 0.15 mm to 3.0 mm, and more preferably 0.3 mm to 2.5 mm. The inside diameter of the dispensing tube 94 is not particularly limited, and is, for example, 0.05 mm to 3.0 mm, preferably 0.1 mm to 2.0 mm, and more preferably 0.15 mm to 1.5 mm. The length of the dispensing tube 94 is not particularly limited, and is preferably a length of not more than 5 times the balloon diameter, for example, 1.0 mm to 50 mm, preferably 3 mm to 40 mm, and more preferably 5 mm to 35 mm.

The control unit 99 is composed, for example, of a computer, and controls the rotation mechanism section 61, the movement mechanism section 80, and the application mechanism section 90. Therefore, the control unit 99 can control the rotating speed of the balloon 30, the moving speed of the dispensing tube 94 in the axial direction of the balloon 30, the drug discharge rate from the dispensing tube 94, and so on.

The coating solution supplied from the dispensing tube 94 to the balloon 30 is a solution or dispersion containing the constituent materials of the coating layer 40, and contains a water-insoluble drug, an excipient, an organic solvent, and water. After the coating solution is supplied to the outer surface of the balloon 30, the organic solvent and water volatilize, whereby a coating layer 40 including a plurality of elongate bodies 42 which are crystals of the water-insoluble drug extending while having independent long axes is formed on the outer surface of the balloon 30.

The viscosity of the coating solution is, for example, 0.5 cP to 1,500 cP, preferably 1.0 cP to 500 cP, and more preferably 1.5 cP to 100 cP.

The water-insoluble drug means a drug which is insoluble or difficultly soluble in water; specifically, the water-insoluble drug is a drug of which the solubility in water, for example, is less than 5 mg/mL at pH 5 to 8. The solubility may be less than, for example, 1 mg/mL, or, further, may be less than 0.1 mg/mL. The water-insoluble drug includes fat-soluble drugs.

Some preferred examples of the water-insoluble drug include immunosuppressants, e.g., cyclosporines inclusive of cyclosporine, immunoadjuvants such as rapamycin, carcinostatics such as paclitaxel, antiviral or antibacterial agents, antineoplastic agents, analgesic and anti-inflammatory agents, antibiotics, antiepileptics, anxiolytic agents, antiparalytic agents, antagonists, neuron blocking agents, anticholinergic and cholinergic agents, muscarine antagonists and muscarine agents, antiadrenergic agents, antiarrhythmic agents, antihypertensive agents, hormone preparations, and nutritional supplements.

The water-insoluble drug is preferably at least one selected from a group composed of rapamycin, paclitaxel, docetaxel, and everolimus. The rapamycin, paclitaxel, docetaxel and everolimus herein include their analogs and/or derivatives so long as the analogs and/or derivatives have equivalent drug activity to the original. For example, paclitaxel and docetaxel are in an analog relation. Rapamycin and everolimus are in a derivative relation. Among these, more preferable is paclitaxel.

The excipient constitutes the base material 41 on the balloon 30. The excipient includes a water-soluble low-molecular compound. The molecular weight of the water-soluble low-molecular compound is, for example, 50 to 2,000, preferably 50 to 1,000, more preferably 50 to 500, and still more preferably 50 to 200. The amount of the water-soluble low-molecular compound is preferably, for example, 5 parts by weight to 10,000 parts by weight, more preferably 5 parts by weight to 200 parts by weight, and still more preferably 8 parts by weight to 150 parts by weight, per 100 parts by weight of the water-insoluble drug. Examples of the applicable constituent material of the water-soluble low-molecular compound include serine ethyl ester, citric acid esters, polysorbates, water-soluble polymers, sugars, contrast agents, amino acid esters, glycerol esters of short-chain monocarboxylic acids, pharmaceutically acceptable salts and surfactants, and mixtures of two or more of these. The water-soluble low-molecular compound is characterized in that the water-soluble low-molecular compound has a hydrophilic group and a hydrophobic group and is soluble in water. Preferably, the water-soluble low-molecular compound is non-swellable or difficultly swellable (i.e., does not easily swell). The excipient is preferably amorphous on the balloon 30. The excipient including the water-soluble low-molecular compound has an effect of uniformly dispersing the water-insoluble drug on the outer surface of the balloon 30. The excipient constituting the base material 41 is preferably not a hydrogel. Being the low-molecular compound, the base material 41 is rapidly dissolved without being swelled upon contact with an aqueous solution. Further, since the base material 41 becomes easily soluble upon inflation of the balloon 30 in a blood vessel, the crystal particles of the water-insoluble drug on the outer surface of the balloon 30 becomes easily releasable; thus, the base material 41 has an effect of increasing the amount of the drug crystal particles adhered to the blood vessel. In the case where the base material 41 is a matrix composed of a contrast agent such as Ultravist®), the crystal particles are embedded in the matrix, and crystals are not produced to extend from the substrate of the balloon 30 toward the outside of the matrix. In accordance with an aspect, the elongate bodies 42 according to the present embodiment extend from the surface of the substrate of the balloon 30 to the outside of the base material 41. The length of that portion of the elongate body 42 which is located on the outside of the base material 41 is greater than the length of that portion of the elongate body 42 which is located inside the base material 41. The base material 41 is formed in such a manner as to support the base portions 45 of the elongate bodies 42 which are crystals.

The organic solvent is not particularly limited, and examples of the organic solvent include tetrahydrofuran, acetone, glycerin, ethanol, methanol, dichloromethane, hexane, and ethyl acetate. Among the organic solvents, preferred are mixed solvents of some of tetrahydrofuran, ethanol, and acetone.

Examples of a mixture of an organic solvent with water include a mixture of tetrahydrofuran and water, a mixture of tetrahydrofuran and ethanol and water, a mixture of tetrahydrofuran and acetone and water, a mixture of acetone and ethanol and water, and a mixture of tetrahydrofuran and acetone and ethanol and water.

A method of forming crystals of the water-insoluble drug on the outer surface of the balloon 30 by use of the above-mentioned balloon coating apparatus 60 will be described below.

First, the inflation fluid is supplied into the balloon 30 through the three-way cock (i.e., three-way valve) connected to the proximal opening portion 27 of the balloon catheter 10. Next, in a state where the balloon 30 is inflated, the three-way cock is operated to seal up the inflation lumen 23, thereby maintaining the balloon 30 in the inflated state. The balloon 30 is inflated with a pressure (e.g., 4 atm) lower than a pressure (e.g., 8 atm) at the time of use in a blood vessel. Note that the coating layer 40 can also be formed on the outer surface of the balloon 30 without inflating the balloon 30, and, in that case, it is unnecessary to supply the inflation fluid into the balloon 30.

Subsequently, in a condition where the dispensing tube 94 does not make contact with the outer surface of the balloon 30, the balloon catheter 10 is rotatably disposed on the support base 70, and the hub 26 is interlocked with the rotation mechanism section 61.

Next, the position of the movable base 81 is adjusted to position the dispensing tube 94 in relation to the balloon 30. In this instance, the dispensing tube 94 is positioned to a position on the most distal side in a surface region of the balloon 30 where to form the coating layer 40. As an example, the extending direction (discharge direction) of the dispensing tube 94 is opposite to the rotating direction of the balloon 30. Therefore, at the position where the dispensing tube 94 is put in contact with the balloon 30, the balloon 30 is rotated in the direction opposite to the discharge direction in which the coating solution is discharged from the dispensing tube 94. By this, a physical stimulus can be given to the coating solution, whereby formation of crystal nuclei of the drug crystal can be promoted. Since the extending direction (discharge direction) of the dispensing tube 94 toward the opening portion 95 is opposite to the rotating direction of the balloon 30, the crystals of the water-insoluble drug formed on the outer surface of the balloon 30 are liable to be formed assuming a morphological form wherein the crystals include a plurality of elongate bodies 42 having mutually independent long axes. Note that the extending direction of the dispensing tube 94 may not necessarily be opposite to the rotating direction of the balloon 30, and, hence, may be the same as or perpendicular to the rotating direction.

Subsequently, the coating solution is supplied to the dispensing tube 94 while adjusting the feed rate by the feed pump 93, the balloon catheter 10 is rotated by the rotation mechanism section 61, and the movable base 81 is moved so that the dispensing tube 94 is gradually moved proximally along the axial direction of the balloon 30. The coating solution discharged from the opening portion 95 of the dispensing tube 94 is applied to the outer surface of the balloon 30 while drawing a spiral, since the dispensing tube 94 is moved relative to the balloon 30.

The moving speed of the dispensing tube 94 is not particularly limited, and is, for example, 0.01 mm/second to 2 mm/second, preferably 0.03 mm/second to 1.5 mm/second, and more preferably 0.05 mm/second to 1.0 mm/second. The discharge rate of the coating solution from the dispensing tube 94 is not particularly limited, and is, for example, 0.01 μL/second to 1.5 μL/second, preferably 0.01 μL/second to 1.0 μL/second, and more preferably 0.03 μL/second to 0.8 μL/second. The rotating speed of the balloon 30 is not particularly limited, and is, for example, 10 rpm (revolutions per minute) to 300 rpm, preferably 30 rpm to 250 rpm, and more preferably 50 rpm to 200 rpm. The diameter of the balloon 30 when coated with the coating solution is not particularly limited, and is, for example, 1 mm to 10 mm, preferably 2 mm to 7 mm.

Thereafter, the organic solvent contained in the coating solution applied to the outer surface of the balloon 30 volatilizes earlier than water. Therefore, the organic solvent volatilizes in a condition where the water-insoluble drug, the water-soluble low-molecular compound and water are left on the surface of the balloon 30. When the organic solvent thus volatilizes with water left in the coating, the water-insoluble drug is precipitated inside the water-soluble low-molecular compound that contains water, and crystals gradually grow from crystal nuclei, so that drug crystals of a morphological form wherein the crystals include a plurality of elongate bodies 42 having mutually independent long axes are formed on the outer surface of the balloon 30. Note that the elongate bodies 42 in this state have not yet been formed with the bent portions 43. The base portions 45 of the elongate bodies 42 may be located on the outer surface of the balloon 30, on the outer surface of the base material 41, or in the inside of the base material 41 (see FIG. 4). After the organic solvent has volatilized and the drug crystals are precipitated as the plurality of elongate bodies 42, water evaporates more slowly than the organic solvent, and the base material 41 including the water-soluble low-molecular compound is formed. The time taken for evaporation of water is appropriately set in accordance with the kind of the drug, the kind of the water-soluble low-molecular compound, the kind of the organic solvent, the ratios of the amounts of the materials, the coating amount of the coating solution, and is, for example, approximately 1 seconds to 600 seconds.

Then, while rotating the balloon 30, the dispensing tube 94 is gradually moved in the axial direction of the balloon 30, whereby the coating layer 40 is gradually formed on the outer surface of the balloon 30 along the axial direction of the balloon 30. After the coating layer 40 including the elongate bodies 42 before bending is formed over the whole range of coating for the balloon 30, operations of the rotation mechanism section 61, the movement mechanism section 80 and the application mechanism section 90 are stopped.

Thereafter, the balloon catheter 10 is removed from the balloon coating apparatus 60, to complete the coating of the balloon 30.

The balloon folding apparatus 100 will be described below. The balloon folding apparatus 100 is an apparatus capable of folding the balloon 30 in the manner of winding around the inner tube 22.

Figure 9:
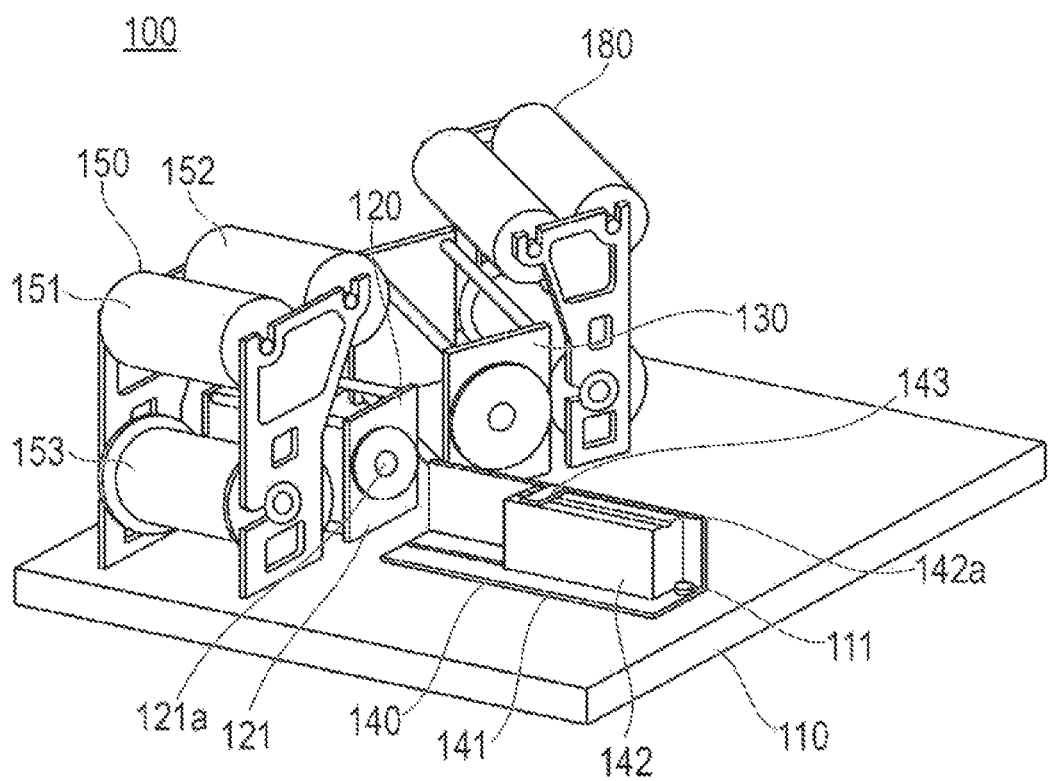
FIG. 9 is a perspective view of a balloon folding apparatus.

As depicted in FIG. 9, the balloon folding apparatus 100 has a pleating section 120, a folding section 130, and a support base 140 disposed on a base 110 formed in a base shape. The pleating section 120 is capable of forming the balloon 30 with wing portions 32 projecting in radial directions. The folding section 130 is capable of folding the wing portions 32 formed in the balloon 30, in the manner of lying flat in the circumferential direction. The support base 140 is capable of mounting and holding the balloon catheter 10 on the support base 140. The wing portions 32 formed in the balloon 30 are formed by pleats extending substantially in an axial direction of the balloon 30, such that the pleats project in the circumferential direction from a long axis of the balloon 30 when viewed in a section perpendicular to the axis of the balloon 30. The length in the long axis direction of the wing portions 32 does not exceed the length of the balloon 30. The length of the wing portions 32 in the direction of projecting in the circumferential direction of the catheter main body 20 is, for example, 1 mm to 8 mm. The number of the wing portions 32 is not particularly limited, it can be selected from among the numbers of two to seven, and the number of wing portions 32 is three in the present embodiment.

On the base 110, a film supply section 150 that supplies a first film 155 and a second film 156 to the pleating section 120 is disposed adjacently to the pleating section 120. In addition, on the base 110, a film supply section 180 that supplies a first film 181 and a second film 182 to the folding section 130 is disposed adjacently to the folding section 130.

The pleating section 120 has a front surface plate 121 perpendicular to the base 110, and the front surface plate 121 has an insertion hole 121a into which a distal portion of the balloon catheter 10 can be inserted. In addition, the folding section 130 has a front surface plate 131 perpendicular to the base 110, and the front surface plate 131 has an insertion hole 131a into which the distal portion of the balloon catheter 10 can be inserted. The front surface plate 131 of the folding section 130 faces in a direction different by a predetermined angle from the direction in which the front surface plate 121 of the pleating section 120 faces.

On that side of the support base 140 which is remote from the pleating section 120 and the folding section 130, a support shaft 111 projecting upward from the base 110 is pivotally mounted. The support base 140, by sliding movement on an upper surface of the base 110 with the support shaft 111 as a center, can be positioned in a position for facing the front surface plate 121 of the pleating section 120 and a position for facing the front surface plate 131 of the folding section 130.

The support base 140 has a base section 141 mounted on the base 110, and a holding base section 142 horizontally movable on the base section 141. The base section 141 is slidable on the upper surface of the base 110. The holding base section 142 can be advanced or retracted in relation to the pleating section 120 or the folding section 130, by sliding movement on the upper surface of the base section 141.

An upper surface of the holding base section 142 is formed with a groove-shaped mounting section 142a on which the catheter main body 20 of the balloon catheter 10 can be mounted. In addition, the holding base section 142 is provided with a holding section 143 in such a manner as to cover a part of the mounting section 142a from above. The holding section 143 is capable of fixing by holding the catheter main body 20 of the balloon catheter 10 mounted on the mounting section 142a. Note that the balloon catheter 10 may be fixed by other methods so long as the balloon catheter 10 can be fixed.

In a state in which the support base 140 faces the front surface plate 121 of the pleating section 120, the center of the insertion hole 121a formed in the front surface plate 121 is located on an extension line of the mounting section 142a of the holding base section 142. Therefore, the balloon catheter 10 with the catheter main body 20 mounted on the mounting section 142a is inserted into the inside of the pleating section 120 through the center position of the insertion hole 121a. In a state in which the support base 140 faces the front surface plate 131 of the folding section 130, the center of the insertion hole 131a formed in the front surface plate 131 is located on an extension line of the mounting section 142a of the holding base section 142. Therefore, the balloon catheter 10 with the catheter main body 20 mounted on the mounting section 142a is inserted into the inside of the folding section 130 through the center position of the insertion hole 131a, by sliding movement of the holding base section 142 on the base section 141.

Figure 10:
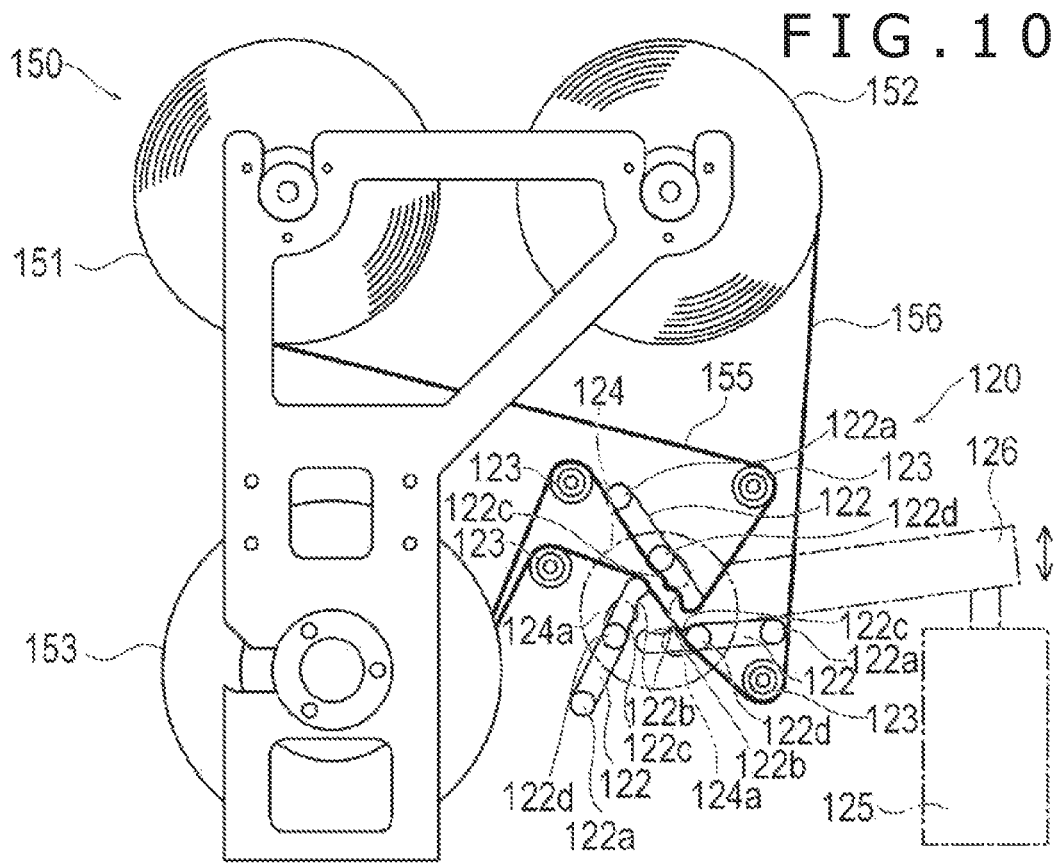
FIG. 10 is a front view depicting the layout of blades of a pleating section and a film supply section.

The structure of the pleating section 120 will be described below. As depicted in FIG. 10, the pleating section 120 has three blades 122 (wing forming members) in the inside of the pleating section. Each of the blades 122 is a plate-shaped member formed to have an equal sectional shape at positions along the axial direction of the balloon catheter 10 inserted. The blades 122 are disposed at mutual angles of 120 degrees, with the center position of the inserted balloon 30 as a reference. In other words, the blades 122 are disposed at regular (or equal) angular intervals along the circumferential direction. The blade 122 has a rotary movement center portion 122a near its outer circumferential end portion, and can be moved rotationally around the rotary movement center portion 122a. In addition, the blade 122 has a moving pin 122d extending in the axial direction, on the inner circumference side relative to the rotary movement center portion 122a. The moving pin 122d is fitted in a fitting groove 124a formed in a rotary member 124 which is rotatable inside the pleating section 120. The rotary member 124 is interlocked to a beam section 126 extending substantially horizontally. The rotary member 124 can be moved rotationally by receiving a rotating force from the beam section 126 which is inclined by receiving a force from a drive source 125 such as a hydraulic cylinder or a motor. When the rotary member 124 is rotated, the moving pins 122d fitted in the fitting grooves 124a are moved in the circumferential direction, whereby each of the blades 122 is moved rotationally around the rotary movement center portion 122a of each of the blades 122. With the three blades 122 rotationally moved, a space region in a central area surrounded by the blades 122 can be narrowed. Note that the number of the blades 122 is not particularly limited so long as it is not less than two.

At an inner circumferential end portions on the side opposite to its rotary movement center portion 122a, the blade 122 has a first shape forming portion 122b and a second shape forming portion 122c. As the blade 122 is moved rotationally, the first shape forming portion 122b attaches to the surface of the balloon 30 inserted in the pleating section 120, whereby the balloon 30 can be formed with the wing portion 32 projecting in a radial direction. As the blade 122 is moved rotationally, the second shape forming section 122c attaches to the wing portion formed in the balloon 30, whereby the wing portion 32 can be curved in a predetermined direction. In addition, the pleating section 120 has a heater (not depicted) for heating the blades 122. The length of the blade 122 along the axial direction of the balloon catheter 10 is greater than the length of the balloon 30. In addition, the lengths of the first shape forming portion 122b and the second shape forming portion 122c of the blade 122 may range or may not range over the whole length of the blade 122.

In accordance with an aspect, the blades 122 are supplied from the film supply section 150 with the first film 155 and the second film 156 which are made of resin. For guiding each of the films, a plurality of rotary shaft portions 123 is provided in the pleating section 120. The first film 155 is passed from a first film holding section 151 and through the rotary shaft section 123, to be engaged on a surface of the blade 122 disposed at an upper portion. In addition, the first film 155 is passed from the blade 122 and through the rotary shaft section 123, to reach a film take-up section 153 which is rotationally driven by a drive source such as a motor (not depicted). The second film 156 is passed from a second film holding section 152 and through the rotary shaft section 123, to be engaged on the two blades 122 disposed at lower portions. In addition, the second film 156 is passed through the rotary shaft section 123, to reach the film take-up section 153. By these, a state is established in which the center position of the pleating section 120 in which the balloon 30 is inserted and passed is surrounded by the first film 155 and the second film 156.

The first film 155 and the second film 156 have a function of protecting the balloon 30 by preventing the balloon 30 from making direct contact with the surfaces of the blades 122 when the balloon 30 is inserted into the pleating section 120 and the blades 122 are moved rotationally to form the balloon 30 with the wing portions 32. After the wing portions 32 of the balloon 30 are formed, the first film 155 and the second film 156 are taken up onto the film take-up section 153 by a predetermined length. In other words, those portions of the first film 155 and the second film 156 which have once made contact with the balloon 30 do not make contact with the balloon 30 again, and, each time the balloon 30 is inserted, new portions of the films are supplied to the center position of the pleating section 120.

Figure 11:
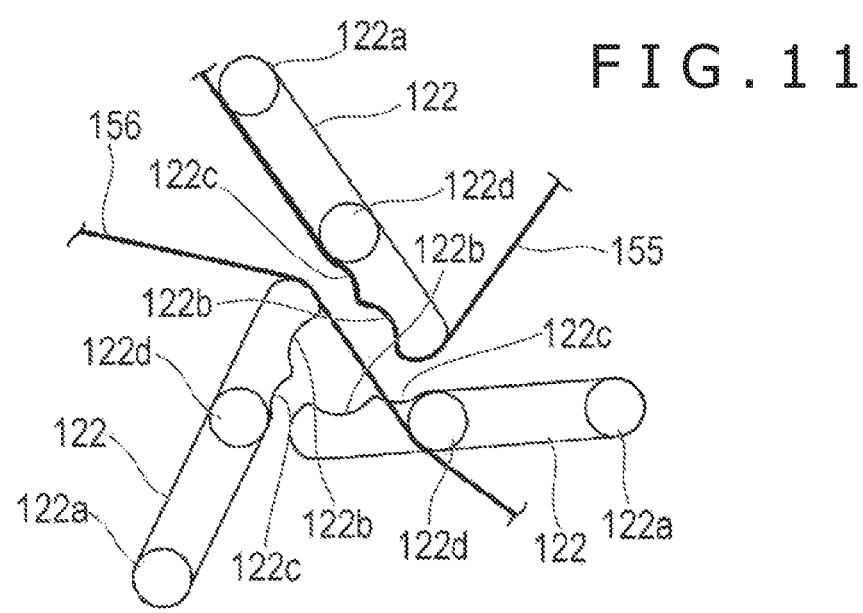
FIG. 11 is a front view of the blades of the pleating section.

As depicted in FIG. 11, in a state before the insertion of the balloon 30, the first shape forming portions 122b and the second shape forming portions 122c of the three blades 122 are spaced from one another. A central region among the blades 122 is surrounded by the respective first shape forming portions 122b which are substantially arcuate (i.e., bowed or curved) in shape, and the balloon 30 before folded can be inserted in the respective shape forming portions 122b.

Figure 12:
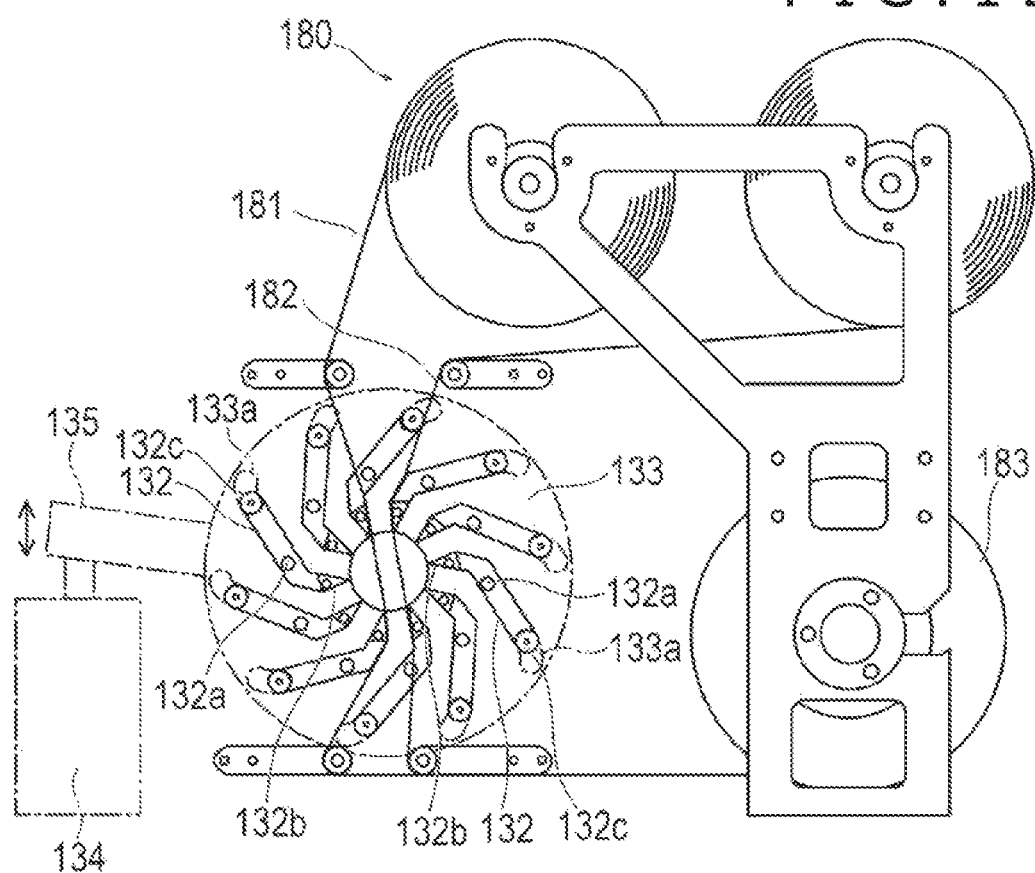
FIG. 12 is a front view depicting the layout of blades in a folding section and a film supply section.

The structure of the folding section 130 will be described below. As depicted in FIG. 12, the folding section 130 has ten blades 132 (folding members) in the inside of the folding section. Each of the blades 132 is a plate-shaped member formed to have an equal sectional shape at positions along the axial direction of the balloon catheter 10 inserted. The blades 132 are disposed at mutual angles of 36 degrees, with the center position of the inserted balloon 30 as a center. In other words, the blades 132 are disposed at regular (or equal) angular intervals along the circumferential direction. The blade 132 has a rotary movement center portion 132a near its center, and can be moved rotationally around the rotary movement center portion 132a. In addition, each blade 132 has a moving pin 132c extending in the axial direction, near an outer circumferential end portion of the blade 132. The moving pin 132c is fitted in a fitting groove 133a formed in a rotary member 133 which is rotatable inside the folding section 130. The rotary member 133 is interlocked to a beam 135 extending substantially horizontally. The rotary member 133 can be moved rotationally by receiving a rotating force from the beam 135 which is inclined by receiving a force from a drive source 134 such as a hydraulic cylinder or a motor. When the rotary member 133 is rotated, the moving pins 132c fitted in the fitting grooves 133a are moved in the circumferential direction, whereby each of the blades 132 is moved rotationally around the rotary movement center portion 132a of each of the blades 132. With the ten blades 132 rotationally moved, a space region in a central area surrounded by the blades 132 can be narrowed. Note that the number of the blades 132 is not limited to ten.

The blade 132 is bent on a distal side, and its distal portion 132b is sharp in shape. As the blades 132 are moved rotationally, the distal portions 132b attaches to the surface of the balloon 30 inserted into the folding section 130, whereby the wing portions 32 formed in the balloon 30 can be folded in the manner of lying flat in the circumferential direction. In addition, the folding section 130 has a heater (not depicted) for heating the blades 132.

The blades 132 are supplied from the film supply section 180 with the first film 181 and the second film 182 which are made of resin. A supplying structure for each film is the same as that in the case of the pleating section 120. The first film 181 and the second film 182 are disposed to face each other such that a central space region surrounded by the blades 132 is interposed between the first film 181 and the second film 182. By the first film 181 and the second film 182, the balloon 30 inserted in the folding section 130 can be prevented from making direct contact with the surfaces of the blades 132. The first film 181 and the second film 182 are passed through the blades 132, to reach a film take-up section 183 which is rotationally driven by a drive source such as a motor not depicted.

Figure 13:
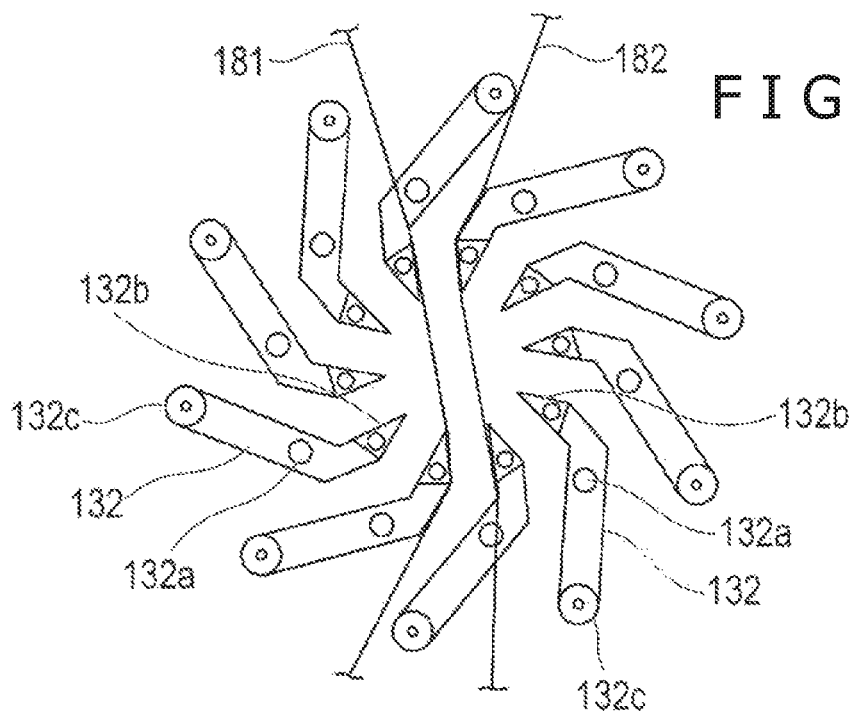
FIG. 13 is a front view of the blades in the folding section.

As depicted in FIG. 13, in a state before insertion of the balloon 30, the distal portions 132b of the blades 132 are in the state of being spaced from one another in the circumferential direction. In a central region which is surrounded by the blades 132 and is located between the first film 181 and the second film 182, the balloon 30 formed with the wing portions 32 can be inserted.

A method of folding the balloon 30 formed on an outer surface of the balloon 30 with crystals of a drug by the balloon coating apparatus 60, by use of the balloon folding apparatus 100, will be described below.

First, for forming the balloon 30 with the wing portions 32, the catheter main body 20 is mounted on the mounting section 142a of the support base 140 and is held by the holding section 143. An inflation fluid is injected into the balloon 30 through a three-way cock (or three-way valve) attached to a hub 26, the hub 26 and the inner tube 22, whereby the balloon 30 is put into a little inflated (i.e., partially inflated) state. In addition, the blades 122 in the pleating section 120 are heated. A core member 62 is inserted in a guide wire lumen 24. By the core member 62, the catheter main body 20 is restrained from flexure due to the weight of catheter main body 20.

Figure 14:
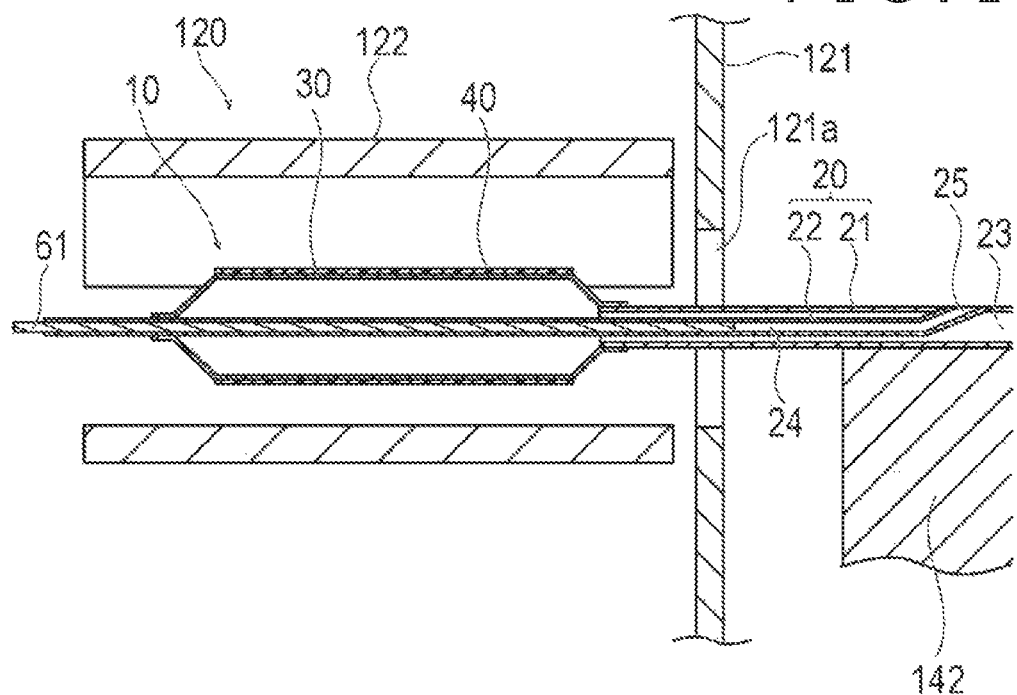
FIG. 14 is a sectional view depicting the balloon catheter disposed in the pleating section.

Next, as depicted in FIG. 14, the holding base section 142 is moved sliding on the base section 141, to insert the balloon catheter 10 into the pleating section 120 through the insertion hole 121a.

Figure 15:
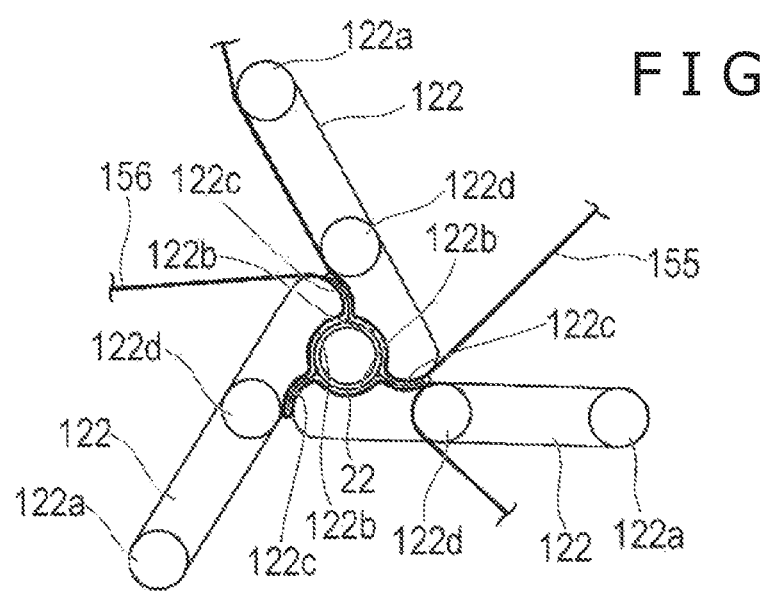
FIG. 15 is a front view depicting the blades in a state in which the balloon is formed with wing portions by moving the blades of the pleating section rotationally.

Subsequently, the drive source 125 is operated to rotate the rotary member 124 (see FIG. 12), whereon as depicted in FIG. 15, the blades 122 are moved rotationally, and the first shape forming portions 122b of the blades 122 approach one another, so that the central region among the blades 122 is narrowed. Attendant on this, the balloon 30 inserted in the central region among the blades 122 is pressed against the inner tube 22 by the first shape forming portions 122b. That portion of the balloon 30 which is not pressed by the first shape forming portion 122b is pushed out into a gap between a distal portion of one blade 122 and the second shape forming portion 122c of the blade 122 adjacent to the one blade 122, whereby the wing portion 32 curved to one side is formed. Since the balloon 30 is heated to approximately 50 degrees to 60 degrees by the blades 122, the wing portions 32 thus formed can maintain their shapes. In this way, the balloon 30 is formed with three wing portions 32 along the circumferential direction.

In this instance, those surfaces of each blade 122 which make contact with the balloon 30 are covered by the first film 155 and the second film 156, so that the balloon 30 does not make direct contact with the surfaces of the blades 122. After the balloon 30 is formed with the wing portions 32, the blades 122 are moved rotationally in the manner of returning into their original positions, and the balloon 30 is withdrawn from the pleating section 120. Note that since the internal volume of the balloon 30 is reduced in the process of pleating, it is preferable to regulate the three-way cock according to the volume reduction, to discharge the inflation fluid to the outside, thereby deflating the balloon 30. By this, an excessive force can be prevented from acting on the balloon 30.

Figure 18A:
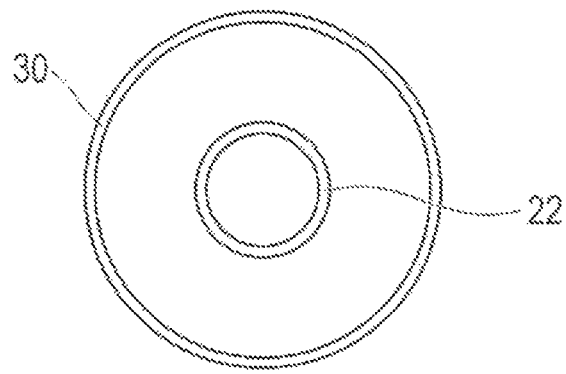
Figure 18B:
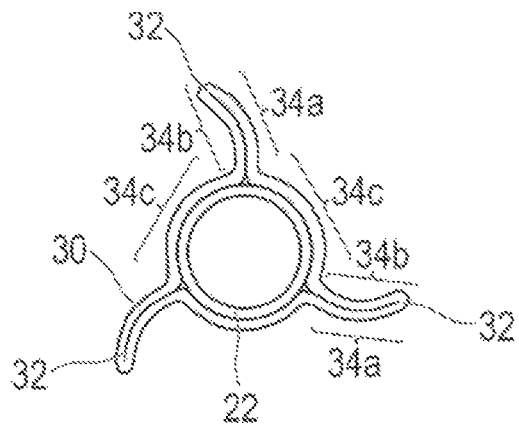

In a state of being filled with the inflation fluid, the balloon 30 is substantially circular in sectional shape, as depicted in FIG. 18A. From this state, the balloon 30 is formed with the projecting wing portions 32, whereby the balloon is formed with: wing outer portions 34a which are pressed by the second shape forming portion 122c and constitute outer surfaces of the wing portions 32; wing inner portions 34b which are pressed by the distal portion of the blade 122 and constitute inner surfaces of the wing portions 32; and intermediate portions 34c which are pressed by the first shape forming portion 122b and are each located between the coating layer wing outer portion 34a and the wing inner portion 34b, as depicted in FIGS. 15 and 18B. Note that in the process of pleating, pressing by the blades 122 is conducted while deflating the balloon 30 for forming the wing portions 32, and, therefore, relatively strong pressing forces by the blades 122 are not needed. Therefore, even when the balloon 30 is pressed by the blades 122, the structure of the crystals formed on the surface of the balloon 30 undergoes relatively little change.

Figure 16:
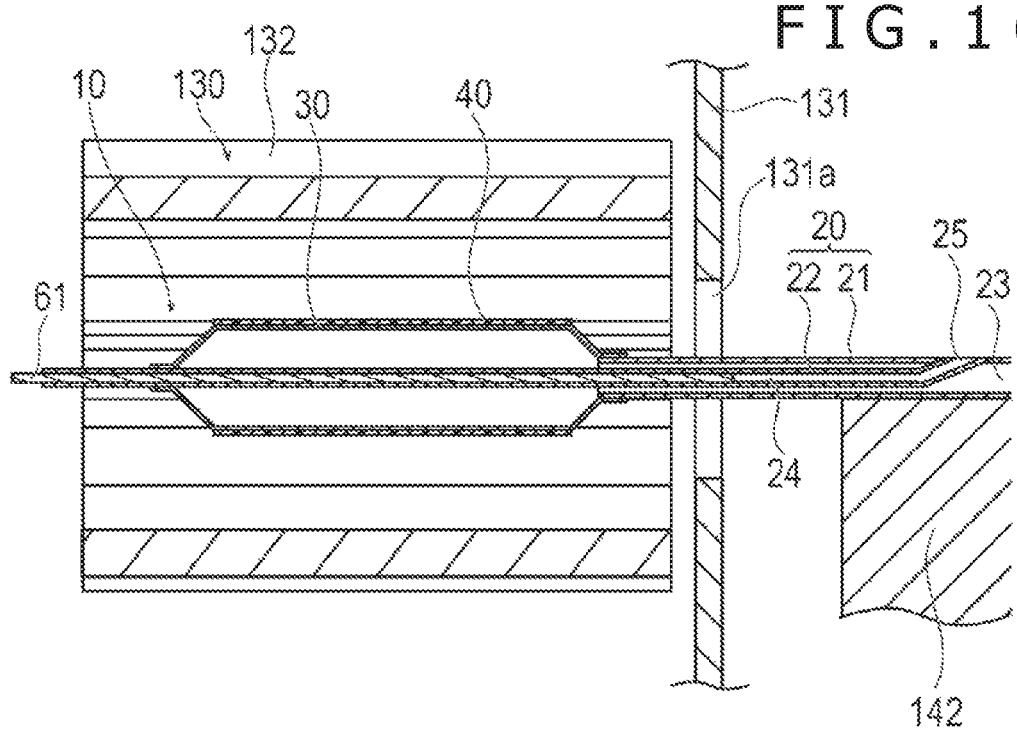
FIG. 16 is a sectional view depicting the balloon catheter disposed in the folding section.

Next, the holding base section 142 is moved on the upper surface of the base section 141 to be spaced from the pleating section 120, and the balloon catheter 10 is withdrawn from the pleating section 120. Subsequently, the support base 140 slides on the upper surface of the base section 110, and the support base 140 is positioned at a position for facing the front surface plate 131 of the folding section 130. Thereafter, the holding base section 142 is moved on the upper surface of the base section 141, whereby the balloon catheter 10 is inserted into the folding section 130 through the insertion hole 131a, as depicted in FIG. 16. In accordance with an aspect, the blades 132 in the folding section 130 are have already been (i.e., preliminarily) heated to approximately 50 degrees to 60 degrees.

Figure 17:
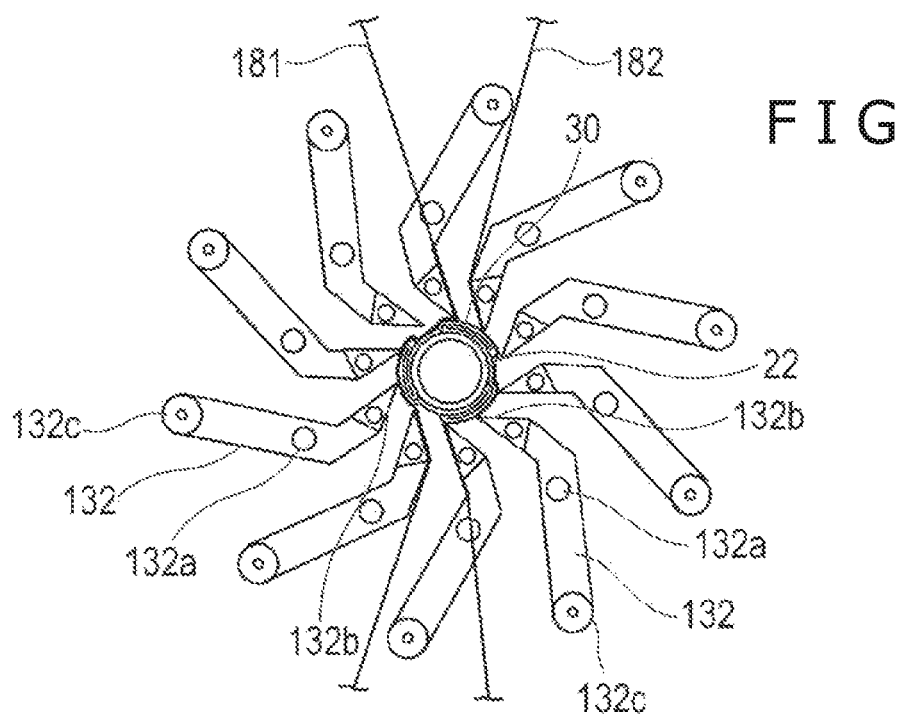
FIG. 17 is a front view depicting the blades in a state in which the wing portions of the balloon are folded by moving the blades in the folding section rotationally.

After the balloon 30 formed with the wing portions 32 is inserted into the folding section 130, the drive source 134 is operated to rotate the rotary member 133, as depicted in FIG. 17, whereon the blades 132 are moved rotationally, and the distal portions 132b of the blades 132 approach one another, so that a central region among the blades 132 is narrowed. Attendant on this, the balloon 30 inserted in the central region among the blades 132 is put into a state in which the wing portions 32 are laid flat in the circumferential direction by the distal portions 132b of the blades 132. Since the blades 132 have preliminarily been heated before insertion of the balloon 30 and the balloon 30 is heated by the blades 132, the wing portions 32 laid flat in the circumferential direction by the blades 132 can maintain their shapes. In this instance, those surfaces of each blade 132 which make contact with the balloon 30 are covered by the first film 181 and the second film 182, so that the balloon 30 does not make direct contact with the surfaces of the blades 132.

Figure 18C:
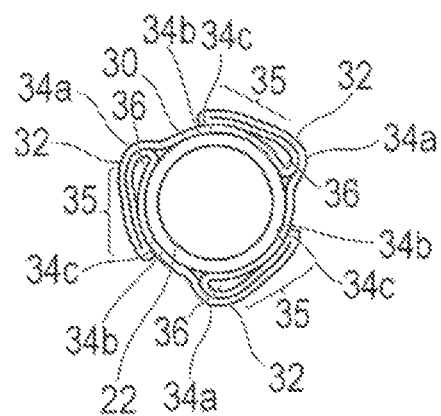

When the wing portions 32 of the balloon 30 are folded, the wing inner portions 34b and the intermediate portions 34c are laid on each other to make contact with each other, to form overlapping portions 35 where portions of the outer surface of the balloon face each other and overlap with each other, as depicted in FIGS. 17 and 18C. In addition, part of the intermediate portions 34c and the wing outer portions 34a are exposed to the outside, without being covered by the wing inner portions 34b. In addition, in the state in which the balloon 30 is folded, a root-side space portion 36 is formed between a root portion of the wing portion 32 and the intermediate portion 34c. In the region of the root-side space portion 36, a minute gap (i.e., extremely small) is formed between the wing portion 32 and the intermediate portion 34c. On the other hand, that region of the wing portion 32 which is on the distal side relative to the root-side space portion 36 is in the state of being in close contact with the intermediate portion 34c. The proportion of the circumferential length of the root-side space portion 36 to the circumferential length of the wing portion 32 is, for example, in the range of 1% to 95%. The wing outer portions 34a of the balloon 30 receive a pressing force in a circumferentially rubbing manner from the first film 181 and the second film 182 pressed by the blades 132, and, further, they are heated. As a result, the elongate bodies 42 of drug crystals provided on the wing outer portions 34a are folded along the circumferential direction, so that bent portions 43 are liable to be formed (see FIG. 3).

In addition, since the portions of the outer surface of the balloon 30 which overlap with each other at the overlapping portions 35 are not exposed to the exterior, pressing forces act thereon indirectly from the blades 132. Therefore, the forces acting on the elongate bodies 42 provided on the portions of the outer surface of the balloon 30 which overlap with each other at the overlapping portions 35 can be easily controlled such as not to become excessively strong. For this reason, it is possible to exert desirable forces for forming the bent portions 43 by folding the elongate bodies 42 provided on the portions of the outer surface of the balloon 30 which overlap with each other at the overlapping portions 35. Accordingly, the elongate bodies 42 having the desirable bent portions 43 are formed on the portions of the outer surface of the balloon 30 which overlap with each other at the overlapping portions 35. In addition, in those regions of the wing inner portion 34b and the intermediate portion 34c facing each other which face the root-side space portion 36, namely, in the regions in which the wing inner portion 34b and the intermediate portion 34c are not in close contact with each other, the elongate bodies 42 are not liable to receive a pressing force. In these regions, therefore, the elongate bodies 42 are not liable to be formed with the bent portion 43. On the other hand, in those regions of the wing inner portions 34b and the intermediate portion 34c facing each other which do not face the root-side space portion 36, namely, in the regions in which the wing inner portion 34b and the intermediate portion 34c are in close contact with each other, the elongate bodies 42 are liable to receive a pressing force. In these regions, therefore, the elongate bodies 42 are liable to be formed with the bent portion 43. Note that where the pressing force, the pressing time and temperature are controlled in such a manner as to help ensure relatively easy formation of the bent portions 43 in the elongate bodies 42 at the overlapping portions 35, the pressing force acting on the wing outer portions 34a may be thereby increased, so that the bent portions 43 may not be formed at the wing outer portions 34a, and, instead, the elongate crystals having long axes may fall down at their roots (i.e., base portion).

After the wing portions 32 of the balloon 30 are folded, the blades 132 are moved rotationally in the manner of returning into their original positions. Next, the balloon 30 is withdrawn from the folding section 130. Subsequently, the holding of the catheter main body 20 by the holding section 143 is released, the balloon 30 is covered by the tubular protective sheath 15 (see FIG. 1), and the folding of the balloon 30 of the balloon catheter 10 is completed. The protective sheath 15 is a member for restraining the drug from falling off the balloon 30, and the protective sheath 15 is removed before the balloon catheter 10 is put to use.

A method of using the balloon catheter 10 according to the present embodiment will be described below, taking as an example a case of treating a stenosed part in a blood vessel.

First, by a known method such as a Seldinger method, the operator percutaneously punctures a blood vessel and places an introducer (not depicted) indwelling. Next, the protective sheath 15 is removed from the balloon catheter 10, priming is performed, and thereafter a guide wire 200 (see FIG. 19) is inserted into the guide wire lumen 24. In this state, the guide wire 200 and the balloon catheter 10 are inserted into the blood vessel through the inside of the introducer. Subsequently, the balloon catheter 10 is moved forward, with the guide wire 200 preceding, and the balloon 30 is delivered to a stenosed 300. Note that a guiding catheter may be used for delivering the balloon catheter 10 to the stenosed part 300.

At the time of moving the balloon 30 within a blood vessel, the overlapping portions 35 where the portions of the outer surface of the balloon 30 overlap with each other are not liable (i.e., likely) to make contact with blood. Therefore, the elongate bodies 42 which are drug crystals located at the overlapping portions 35 are not exposed to the blood, release of the drug crystals into the blood is restrained (or prevented), and the drug crystals can be effectively delivered to the target position.

Figure 19:
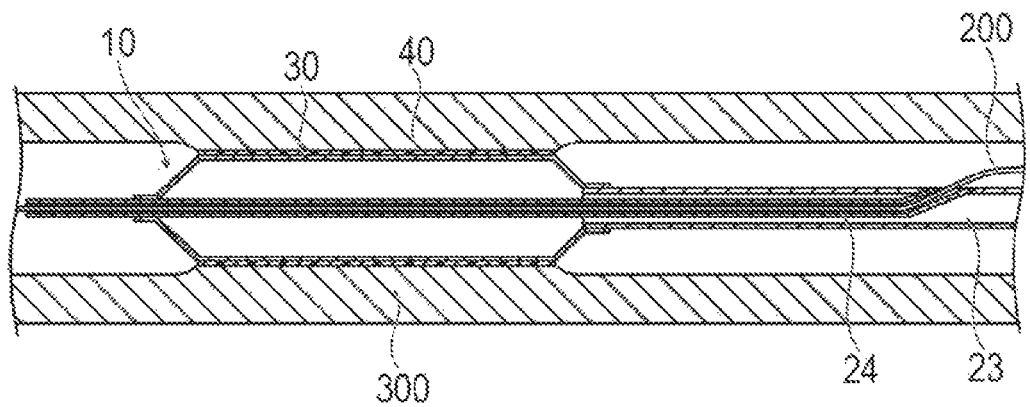
FIG. 19 is a sectional view depicting a state in which a stenosed part of a blood vessel is pushed wide open by the balloon catheter according to the present embodiment.

After the balloon 30 is disposed at the stenosed part 300, a predetermined quantity of an inflation fluid is fed from the proximal opening portion 27 of the hub 26 into the balloon 30 through the inflation lumen 23 by use, for example, of an indeflator or a syringe. By this, the folded balloon 30 is inflated, and the stenosed part 300 is pushed wide open (i.e., widened) by the balloon 30, as depicted in FIG. 19. In this instance, the coating layer 40 containing the drug crystals provided on the outer surface of the balloon 30 makes contact with the stenosed part 300. Since the elongate bodies 42 which are drug crystals contained in the coating layer 40 are bent at the bent portions 43, as depicted in FIG. 4, the density of the crystals on the outer surface of the balloon 30 is relatively higher as compared to that in the case where the elongate bodies 42 are not bent. Therefore, the surface area of the crystals making contact with the stenosed part 300 can be enlarged, and the drug can be effectively delivered from the outer surface of the balloon 30 to the stenosed part 300. Consequently, restenosis of the stenosed part 300 can be effectively restrained.

When the balloon 30 is inflated and the coating layer 40 is thereby pressed against the living body tissue, the base material 41 composed of the water-soluble low-molecular compound contained in the coating layer 40 can be dissolved gradually or rapidly, and, while the dissolution proceeds, the drug is delivered to the living body. Since the elongate bodies 42A, 42B, and 42C which are crystals of the drug differ in the position of their base portions 45 relative to the base material 41, the crystals of the drug differ in living body tissue deliverability as the base material 41 is dissolved gradually or rapidly. In addition, the inflation of the balloon 30 causes cracking of the base material 41, which facilitates dissolution of the base material 41, thereby enabling the elongate bodies 42 as the drug crystals to be relatively easily released from the base material 41. For this reason, where the elongate bodies 42A, 42B, and 42C differing in solubility are provided by adjusting the positions of the base portions 45 of the elongate bodies 42, the tissue deliverability of the drug can be arbitrarily set.

Thereafter, the inflation fluid is discharged by drawing the inflation fluid via the proximal opening portion 27 of the hub 26, whereby the balloon 30 is deflated and put into a folded state. Thereafter, the guide wire 200 and the balloon catheter 10 are drawn out of the blood vessel through the introducer, to complete the procedure.

As has been described above, the balloon catheter 10 according to the present embodiment is a catheter provided on the outer surface of the balloon 30 with the plurality of elongate bodies 42 which are independent crystals of a water-insoluble drug extending in an elongate form, wherein the elongate bodies 42 have bent portions 43 bent relative to the extending direction of the elongated bodies 42. In the balloon catheter 10 configured in this way, since the elongate bodies 42 as the crystals of the water-insoluble drug are bent at the bent portions 43, the density of the crystals on the outer surface of the balloon 30 becomes relatively higher, so that the surface area of the crystals making contact with the living body tissue becomes large. Therefore, releasability of the drug from the outer surface of the balloon 30 and transferability of the drug to the living body tissue can be enhanced, and the drug can be effectively delivered to the living body tissue.

In addition, the balloon 30 has the overlapping portions 35 where portions of the outer surface of the balloon 30 overlap with each other when the balloon 30 is folded in a deflated state, and the elongate bodies 42 having the bent portions 43 are provided on the portions of the outer surface of the balloon 30 which overlap with each other at the overlapping portions 35. As a result, the elongate bodies 42 having the bent portions 43 are not exposed to the exterior in the deflected state, and, therefore, the elongate bodies 42 having the bent portions 43 can be protected until the balloon 30 is delivered to a target position. Accordingly, the drug can be restrained or prevented from falling off the outer surface of the balloon 30 or flowing away into blood stream during delivery, and the drug can be delivered to the living body tissue more effectively.

In addition, the water-insoluble drug may be rapamycin, paclitaxel, docetaxel or everolimus. By this, restenosis of a stenosed part in a blood vessel can be favorably restrained by the elongate bodies 42 having the bent portions 43.

In addition, the method of manufacturing the balloon catheter 10 according to the present embodiment is a method of manufacturing a balloon catheter 10 having on the outer surface of the balloon 30 a plurality of elongate bodies 42 which are crystals of a water-insoluble drug extending while having independent long axes, the method including the steps of: forming the elongate bodies 42 on the outer surface of the balloon 30; forming the balloon 30 with wing portions 32 projecting in radial directions; and folding the wing portions 32 formed in the balloon 30 along the circumferential direction, wherein in at least one of the step of forming the wing portions 32 and the step of folding the wing portions 32, the elongate bodies 42 are bent relative to the extending direction of the elongate bodies 42 by forces for deforming the balloon 30. By the method of manufacturing the balloon catheter 10 configured as above, the elongate bodies 42 can be efficiently formed with the bent portions 43 by utilizing the forces acting on the balloon 30 in the step of forming the balloon 30 with the wing portions 32 or in the step of folding the wing portions 32.

In addition, in the step of folding the wing portions 32, the overlapping portions 35 are formed where portions of the outer surface of the balloon 30 face each other and overlap with each other, and the elongate bodies 42 provided at the portions of the outer surface facing each other at the overlapping portions 35 are bent relative to the extending direction of the elongate bodies 42, whereby the bent portions 43 can be formed, which helps ensure that the forces exerted on the balloon 30 for folding the wing portions 32 act indirectly on the overlapping portions 35, so that the forces acting on the elongate bodies 42 can be controlled. In other words, in regard of the outer surface of the balloon 30 located at the overlapping portions 35, not only a state in which external forces act on the outer surface of the balloon 30 but also a state in which external forces hardly act on the outer surface of the balloon 30 can be realized. For this reason, desirable forces for bending the elongate bodies 42 can easily be exerted on the balloon 30.

In addition, the present disclosure also includes a treatment method (therapy) method of delivering a drug to a lesion affected area in a body lumen by use of the aforementioned balloon catheter 10. The treatment method includes the steps of: inserting the balloon 30 into the body lumen to deliver the balloon 30 to the lesion affected area; inflating the balloon 30 to press the elongate bodies 42 provided with the bent portions 43 against the living body tissue; and deflating the balloon 30 and withdrawing the balloon 30 form the body lumen. According to the treatment method configured in this way, since the balloon 30 has a relatively high density of the crystals on the outer surface of the balloon 30 due to the elongate bodies 42 having the bent portions 43 is pressed against the living body tissue, the surface area of the crystals making contact with the living body tissue is enlarged (i.e., relatively larger). Therefore, releasing property of the drug from the outer surface of the balloon 30 and transferability of the drug to the living body tissue can be enhanced, and the drug can be effectively delivered to the living body tissue.

Note that while the elongate bodies 42 formed on the outer surface of the balloon 30 are bent in the process of folding of the balloon 30 in the present embodiment, the elongate bodies 42 may be bent by pressing by the blades 122 in the process of pleating (see FIG. 15).

Figure 20:
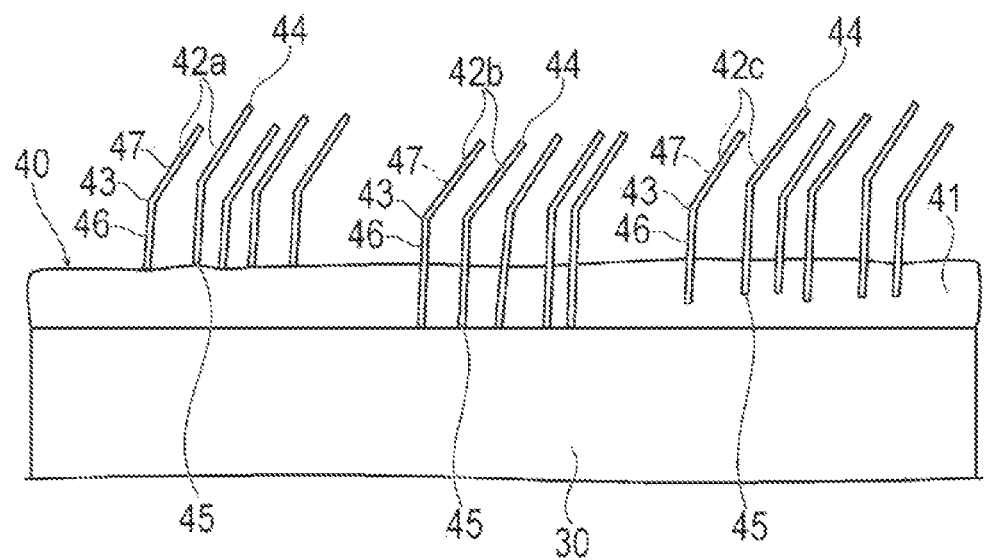
FIG. 20 is a schematic view of elongate bodies and a base material in the case where the base material is film-shaped and amorphous.
Figure 22:
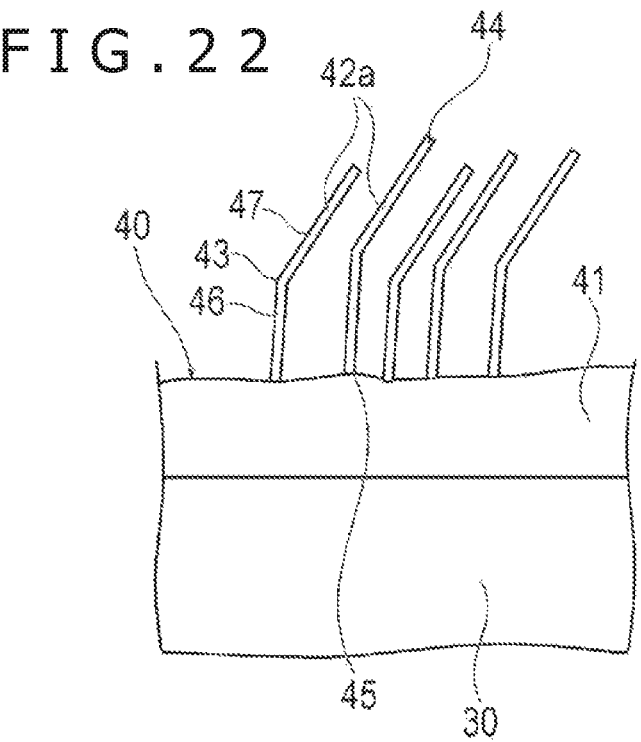
FIG. 22 is a schematic view of first elongate bodies and the base material on the outer surface of the balloon.
Figure 23:
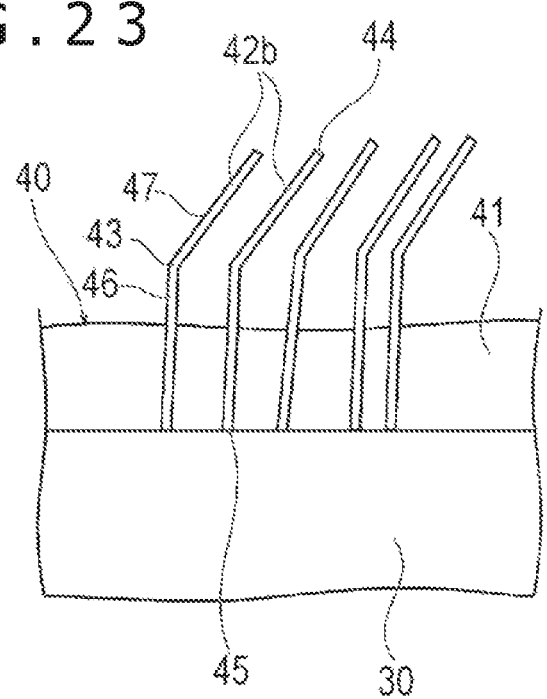
FIG. 23 is a schematic view of second elongate bodies and the base material on the outer surface of the balloon.
Figure 24:
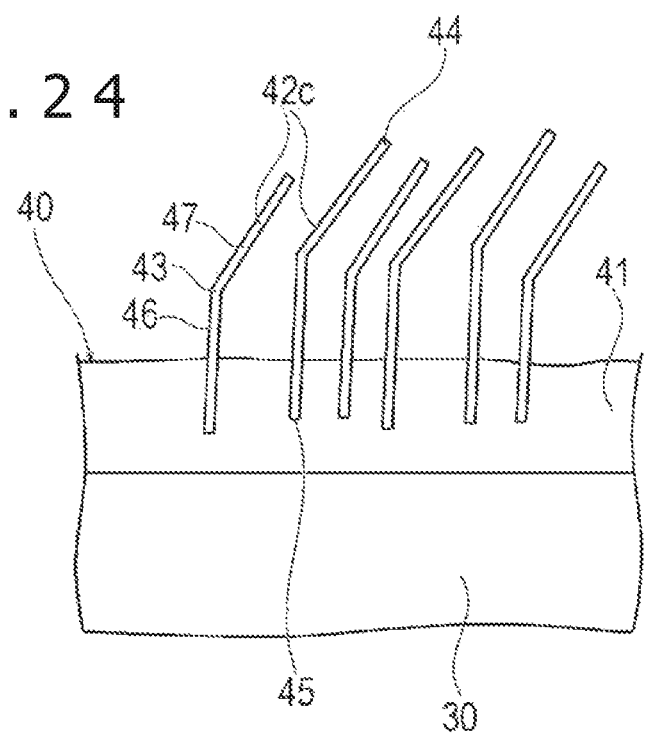
FIG. 24 is a schematic view of third elongate bodies and the base material on the outer surface of the balloon.

In addition, as aforementioned, the base material 41 is present as an amorphous phase, crystal particles, or a mixture of the amorphous phase and the crystal particles. While the base material 41 in FIG. 4 is in a state of crystal particles and/or a particulate amorphous phase, the base material 41 may be in a film-shaped amorphous state, as depicted in FIG. 20. As depicted in FIG. 22, the first elongate bodies 42a extend from the outer surface of the base material 41 toward an outside of the surface. As depicted in FIG. 23, the second elongate bodies 42b extend from the outer surface of the balloon 30 to the exterior of the base material 41 by penetrating the base material 41. As depicted in FIG. 24, the third elongate bodies 42c extend from the inside of the base material 41 to the outside of the base material 41.

Figure 21A:
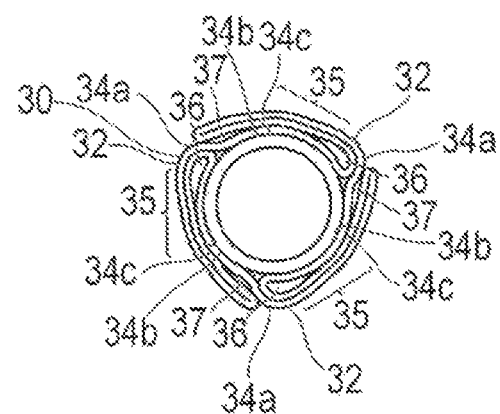
FIGS. 21A and 21B depict sectional views of a balloon in a folded state which has different-shaped wing portions.
Figure 21B:
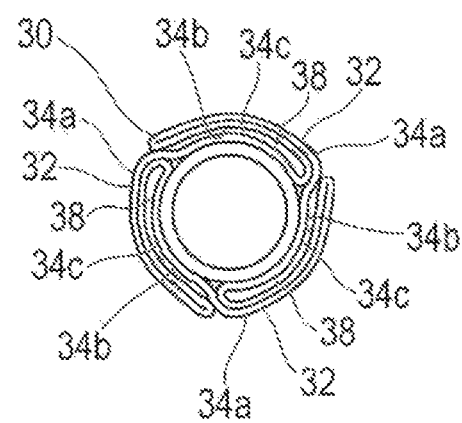

In addition, while the distal ends of the wing portions 32 of the folded balloon 30 do not reach the adjacent wing portions 32 in the present embodiment, the distal ends of the wing portions 32 may reach the adjacent wing portions 32, as in two examples depicted in FIGS. 21A and 21B. In the example in FIG. 21A, a root-side space portion 36 is formed between the root side and the intermediate portion 34c of the wing portion 32, and a distal-side space portion 37 is formed between the distal side and the intermediate portion 34c of the wing portion 32. In this case, in those regions of the wing inner portion 34b and the intermediate portion 34c which face the root-side space portion 36 and the distal-side space portion 37, namely, in the regions in which the wing inner portion 34b and the intermediate portion 34c are not in close contact with each other, the elongate bodies 42 are not liable (i.e., not likely) to receive a pressing force. In the regions in which the wing inner portion 34b and the intermediate portion 34c are not in close contact with each other, therefore, the elongate bodies 42 are not liable (likely) to be formed with the bent portion 43. On the other hand, in those regions of the wing inner portion 34b and the intermediate portion 34c which do not face the root-side space portion 36 or the distal-side space portion 37, namely, in the regions in which the wing inner portion 34b and the intermediate portion 34c are in close contact with each other, the elongate bodies 42 are liable to receive a pressing force. In the regions in which the wing inner portion 34b and the intermediate portion 34c are in close contact with each other, therefore, the elongate bodies 42 are liable (likely) to be formed with the bent portion 43.

In the example in FIG. 21B, over the whole part of the region from the root side of the wing portion 32 to the adjacent wing portion 32, the space portion 38 is formed between the wing portion 32 and the intermediate portion 34c. In this case, in the whole part of the regions of the wing inner portion 34b and the intermediate portion 34c facing each other, the elongate bodies 42 are liable (likely) to receive a pressing force. In the regions of the wing inner portion 34b and the intermediate portion 34c facing each other, therefore, the elongate bodies 42 are not liable (likely) to be formed with the bent portion 43.

In addition, the balloon folding apparatus 100 also may not be used, for folding the balloon 30.

In addition, the coating layer on the outer surface of the balloon 30 may not be provided with the base material which is an excipient.

Figure 25:
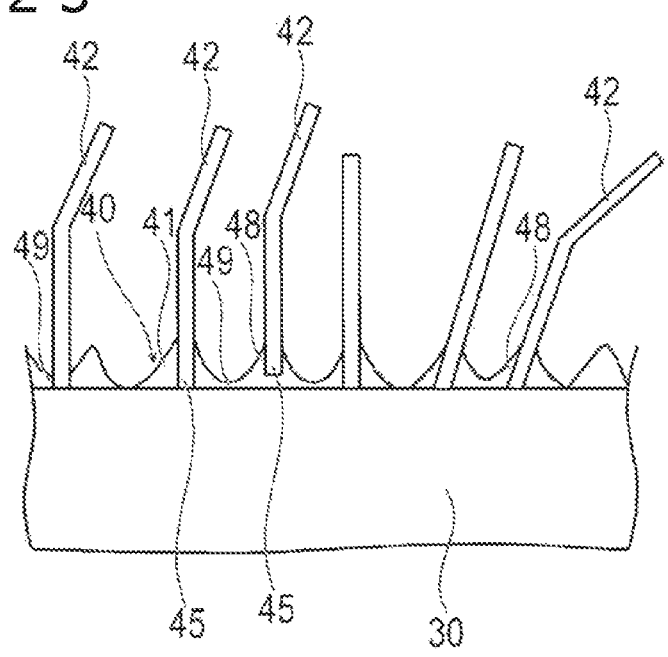
FIG. 25 is a schematic view of elongate bodies and the base material on the outer surface of the balloon.

In addition, as depicted in FIG. 25, the base material 41 which is an additive layer may have projections and recesses (i.e., ruggedness). The height of the projections of the projections and recesses can be, for example, 0.1 µm to 5 µm. The elongate bodies 42 which are crystals are projecting from projecting portions 48 that constitute the projections and recesses (i.e., ruggedness) of the base material 41. In other words, the elongate bodies 42 which are crystals are supported by the projecting portions 48 of the base material 41. Note that the base material 41 may have the projecting portions 48 from which the elongate bodies 42 are not projecting. The elongate bodies 42 which are crystals may project from recessed portions 49 that constitute the ruggedness of the base material 41. The base material 41 may have both the projecting portions 48 which support the elongate bodies 42 and the projecting portions 48 which do not support the elongate bodies 42. The base material 41 may have both the recessed portions 49 which support the elongate bodies 42 and the recessed portions 49 which do not support the elongate bodies 42. In addition, the base material 41 may have both the projecting portions 48 which support the elongate bodies 42 and the recessed portions 49 which support the elongate bodies 42. The elongate bodies 42 may project obliquely from the base material 41 such as to be inclined relative to the outer surface of the balloon 30. The base material 41 may have both the elongate bodies 42 which are substantially perpendicular to the outer surface of the balloon 30 and the elongate bodies 42 which are inclined relative to the outer surface of the balloon 30. The base portions 45 of the elongate bodies 42 may be in direct contact with the outer surface of the balloon 30. Alternatively, the base portions 45 of the elongate bodies 42 may be located in the inside of the base material 41, without making contact with the outer surface of the balloon 30. The base material 41 may have both the elongate bodies 42 which are in direct contact with the outer surface of the balloon 30 and the elongate bodies 42 which are not in contact with the outer surface of the balloon 30.

Second Embodiment

A balloon catheter according to a second embodiment of the present disclosure differs from that of the first embodiment only in the structure of a plurality of elongate bodies 52 which are crystals of a water-insoluble drug. Note that the parts having the same functions as those in the first embodiment above are denoted by the same reference symbols as used above, and descriptions of them will be omitted.

Figure 26:
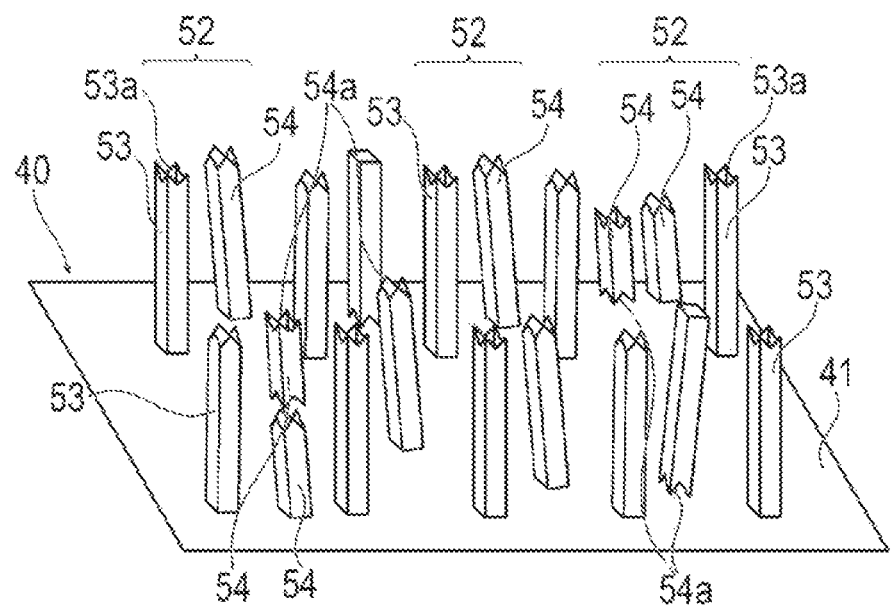
FIG. 26 is a schematic perspective view depicting elongate bodies composed of drug crystals on an outer surface of a balloon according to a second embodiment.
Figure 27:
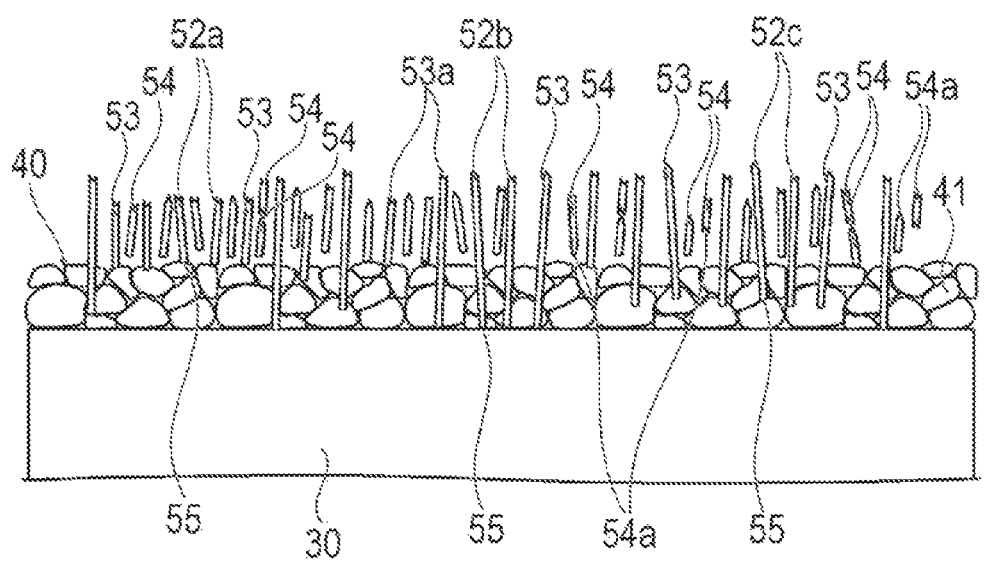
FIG. 27 is a schematic view of the elongate bodies composed of drug crystals and a base material on the outer surface of the balloon according to the second embodiment.
Figure 28:
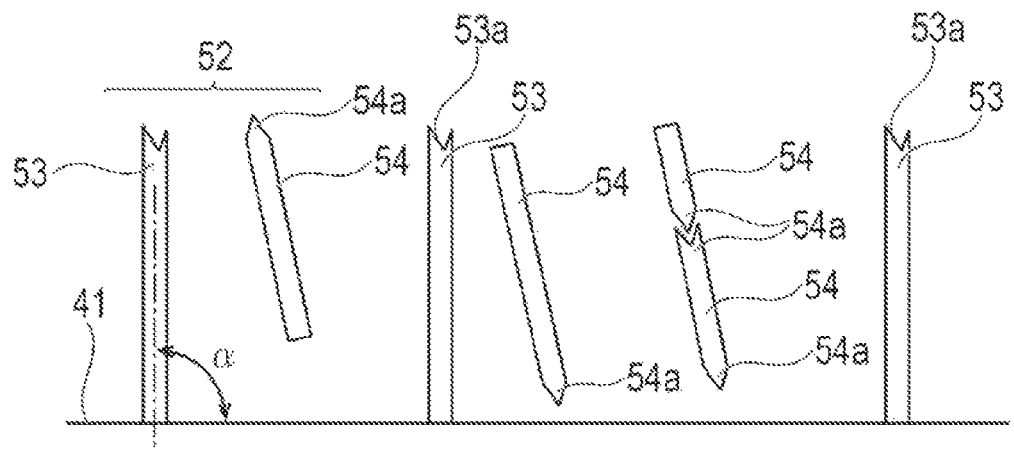
FIG. 28 is a schematic view of the elongate bodies composed of the drug crystals on the outer surface of the balloon according to the second embodiment.

As depicted in FIGS. 26 to 28, the elongate bodies 52 provided in a coating layer 40 on a balloon 30 include first elongate bodies 52a extending from an outer surface of a base material 41 toward the outside of the surface, second elongate bodies 52b extending from an outer surface of the balloon 30 to the outside of the base material 41 by penetrating the base material 41, and third elongate bodies 52c extending from the inside of the base material 41 to the outside of the base material 41. In other words, base portions 55 of the elongate bodies 52 may be in direct contact with the outer surface of the balloon 30, or may not be in direct contact with the outer surface but, instead, the base material 41 (excipient) may exist between the elongate bodies 52 and the outer surface of the balloon 30. The elongate bodies 52a, 52b, and 52c are different in deliverability of a drug to a living body, and, therefore, it is possible, by regulating the positions of the base portions 55 of the crystals of the drug, to arbitrarily control the deliverability of the drug.

In addition, the elongate bodies 52a, 52b and 52c include fixed-side elongate bodies 53 (balloon base material contact crystal particles) which are fixed to the coating layer 40 side, and top-side elongate bodies 54 (balloon base material non-contact crystal particles) in which crystals having long axes are broken and which are separate from the fixed-side elongate bodies 53. The top-side elongate bodies 54 are not continuous with, but are physically independent of, the fixed-side elongate bodies 53. The top-side elongate bodies 54 are held by being located between (in the gaps among) the plurality of fixed-side elongate bodies 53 standing together. Therefore, the density of the crystals on the outer surface of the balloon 30 is enhanced, and the surface area of the crystals making contact with living body tissue can be enlarged. For this reason, releasing property of the drug from the outer surface of the balloon 30 and transferability of the drug to the living body tissue can be enhanced, and the drug can be delivered to the living body tissue more effectively. Of the top-side elongate bodies 54, end portions 54a formed by breakage of the elongate crystals may be oriented toward the surface side of the balloon 30 (toward the coating layer 40 side) or may be oriented toward a radially outer side of the balloon 30 (toward the side opposite to the coating layer 40 side). The directions (the directions of the long axes) of the top-side elongate bodies 54 may be different, and, therefore, may be regular or irregular. In addition, the top-side elongate bodies 54 may be separated from the fixed-side elongate bodies 53 and may be split in plurality. End portions 53a of the fixed-side elongate bodies 53, formed by segmentation (division) of the top-side elongate bodies 54, and end portions 54a of the top-side elongate bodies 54 can be formed to be sharp by breakage of the crystals having long axes. Since the end portions 53a of the fixed-side elongate bodies 53 and the end portions 54a of the top-side elongate bodies 54 are sharp, therefore, it is relatively easy for the fixed-side elongate body 53 and the top-side elongate body 54 to pierce the living body tissue, so that the deliverability of the drug to the living body tissue can be enhanced. Preparation may be made such that almost only the elongate bodies 52b exist on the surface of the balloon 30. Preparation may be made such that almost the elongate bodies 52c exist on the surface of the balloon 30. In addition, preparation may be made such that a combination of a plurality of kinds of the elongate bodies exist on the surface of the balloon 30. For example, a combination of the elongate bodies 52a with the elongate bodies 52b, a combination of the elongate bodies 52b with the elongate bodies 52c, and a combination of the elongate bodies 52c with the elongate bodies 52a may be mentioned. Preparation may be made such that all the elongate bodies 52a, 52b, and 52c exist on the surface of the balloon 30.

The end portions 54a of the top-side elongate bodies 54 may make contact with or may not make contact with the base material 41 of the coating layer 40 located on the outer surface of the balloon 30. In the case where the end portions 54a of the top-side elongate bodies 54 make contact with the base material 41, the positions of the top-side elongate bodies 54 can be stabilized.

The pluralities of fixed-side elongate bodies 53 and top-side elongate bodies 54 may be disposed regularly, or may be disposed irregularly, on the outer surface of the balloon 30. In addition, the fixed-side elongate bodies 53 and the top-side elongate bodies 54 may be provided throughout the coating layer 40 or may be provided in part of the coating layer 40. It is not necessary that all the elongate bodies 52 having the independent long axes should be separated into the fixed-side elongate bodies 53 and the top-side elongate bodies 54; therefore, the elongate bodies 52 which are not separated into the fixed-side elongate bodies 53 and the top-side elongate bodies 54 can exist simultaneously.

The inclination angle α of the fixed-side elongate bodies 53 relative to the outer surface of the balloon 30 or the base material 41 is not particularly limited, and can be, for example, 45 degrees to 135 degrees, preferably 60 degrees to 120 degrees, more preferably 75 degrees to 105 degrees, and still more preferably 90 degrees.

The amount of the drug contained in the coating layer 40 is not particularly limited; the amount in density can be, for example, 0.1 µg/mm$^2$ to 10 µg/mm$^2$, preferably 0.5 µg/mm$^2$ to 5 µg/mm$^2$, more preferably 0.5 µg/mm$^2$ to 3.5 µg/mm$^2$, and still more preferably 1.0 µg/mm$^2$ to 3 µg/mm$^2$. The amount of the crystals in the coating layer 40 is not particularly limited, and the amount of the crystals in the coating layer 40 can be, for example, preferably 5 crystals/(10 µm$^2$) to 500,000 crystals/(10 µm$^2$) (the number of crystals per 10 µm$^2$), more preferably 50 crystals/(10 µm$^2$) to 50,000 crystals/(10 µm$^2$), and still more preferably 500 crystals/(10 µm$^2$) to 5,000 crystals (10 µm$^2$).

The plurality of elongate bodies 52 wherein the crystals have mutually independent long axes may be present in a state where they are combined. The plurality of adjacent elongate bodies 52 may be present in contact with one another while forming different angles between the plurality of adjacent elongate bodies 52. The plurality of elongate bodies 52 may be located with spaces (spaces in which the crystal is not contained) between the plurality of adjacent elongate bodies 52 on the balloon surface. The plurality of elongate bodies 52 may be arranged in a circumferential and brush-like pattern while having different long axis directions. The elongate bodies 52 each exist independently, each have a certain length, and one end (proximal end) of the length portion of each of the elongate bodies 52 is fixed to the base material 41 or the balloon 30. The elongate body 52 does not form a composite structure, and is not interlocked, with the adjacent elongate bodies 52. The long axes of the crystals are almost rectilinear. The elongate bodies 52 form predetermined angles relative to the surface which their long axes intersect and with which their base portions 55 make contact.

The elongate bodies 52 may be hollow or may be solid. In the case where the elongate body 52 is hollow, at least a portion of the elongate bodies 52 near the tip end of the elongated body 52 is hollow. A section of the elongate body 52 in a plane perpendicular (orthogonal) to the long axis of the elongate body 52 has a void (hollow portion). In the elongate body 52 having a void, the section of the elongate body 52 in a plane perpendicular (orthogonal) to the long axis is polygonal in shape. The polygon here is, for example, a triangle, a tetragon, a pentagon, or a hexagon. Therefore, the elongate bodies 52 are each formed as an elongate polyhedron which has a distal end (or a distal surface) and a proximal end (or a proximal surface) and in which a side surface portion between the distal end (or the distal surface) and the proximal end (or the proximal surface) is composed of a plurality of substantially plain surfaces. This crystalline morphological form (hollow elongate body crystalline morphological form) constitutes the whole part or at least part of a plane, at the surface with which the base portions 55 make contact.

The length in the long axis direction of the elongate bodies 52 having the long axes is preferably, for example, 5 µm to 20 µm, more preferably 9 µm to 11 µm, and still more preferably around 10 µm. The diameter of the elongate bodies 52 having the long axes is preferably, for example, 0.01 µm to 5 µm, more preferably 0.05 µm to 4 µm, and still more preferably 0.1 µm to 3 µm. Examples of the combination of length in the long axis direction and diameter of the elongate bodies 52 having the long axes include a combination of a diameter of, for example, 0.01 µm to 5 µm when the length is, for example, 5 µm to 20 µm, a combination of a diameter of, for example, 0.05 µm to 4 µm when the length is, for example, 5 µm to 20 µm, and a combination of a diameter of, for example, 0.1 µm to 3 µm when the length is, for example, 5 µm to 20 µm. The elongate bodies 52 having the long axes may be rectilinear in the long axis direction of the elongate bodies 52, and may also be curved in curved line forms.

The crystalline morphological form including the crystal particles having the long axes as above-mentioned accounts, for example, for at least 50% by volume, and more preferably at least 70% by volume, based on the whole of the drug crystals on the outer surface of the balloon 30.

The crystal particles having the long axes after the coating of the coating layer 40 and before the separation of the elongate bodies 52 into the fixed-side elongate bodies 53 and the top-side elongate bodies 54 are formed not to lie flat but to stand in relation to the outer surface of the balloon 30. In the crystal particles in this instance, the angle of the crystal particle is changed by the pleating (the step of forming the balloon with the wing portions 32) or the folding (the step of folding the wing portions 32) of the balloon 30, whereby the angles of the long axes of the crystal particles relative to the outer surface of the balloon 30 can be changed. Therefore, while the crystals which are formed in the manner of lying flat on the outer surface of the balloon 30 from the beginning are firmly attached (fixed) to the outer surface of the balloon 30 and the adjacent crystal particles, the crystal particles which are standing are not formed in the state of being physically fixed to the outer surface of the balloon 30 or the adjacent crystal particles. For this reason, the standing crystal particles are only positioned (arranged) in such a manner as to make contact with, for example, the outer surface of the balloon 30 or the adjacent crystal particles, and the positions of the outer surface of the balloon 30 or the adjacent crystal particles can be changed on a three-dimensional basis. Accordingly, the crystal particles after the coating are formed such that their angles and positions can be changed through the pleating or folding of the balloon 30. Part of the crystal particles may be embedded in the surface of the balloon 30.

The coating layer 40 including the elongate bodies 52 is formed by the same or similar method to that in the first embodiment. Thus, first, by the balloon coating apparatus 60 (see FIG. 7), the elongate bodies 52 before separated into the fixed-side elongate bodies 53 and the top-side elongate bodies 54 are formed. Thereafter, the wing portions 32 of the balloon 30 are folded by the balloon folding apparatus 100 (see FIG. 9), whereby the elongate bodies 52 are separated into the fixed-side elongate bodies 53 and the top-side elongate bodies 54.

When the wing portions 32 of the balloon 30 are folded, the wing inner portions 34b and the intermediate portions 34c are laid on each other to make contact with each other, to form overlapping portions 35 where portions of the outer surface of the balloon face each other and overlap with each other, as depicted in FIGS. 17 and 18C. In addition, part of the intermediate portions 34c and the wing outer portions 34a are exposed to the outside, without being covered by the wing inner portions 34b. In addition, in the state in which the balloon 30 is folded, a root-side space portion 36 is formed between a root portion of the wing portion 32 and the intermediate portion 34c. In the region of the root-side space portion 36, a minute (i.e., extremely small) gap is formed between the wing portion 32 and the intermediate portion 34c. On the other hand, that region of the wing portion 32 which is on the distal side relative to the root-side space portion 36 is in the state of being in close contact with the intermediate portion 34c. The proportion of the circumferential length of the root-side space portion 36 to the circumferential length of the wing portion 32 is in the range of, for example, 1% to 95%. The wing outer portions 34a of the balloon 30 receive a pressing force in a circumferentially rubbing manner from the first film 181 and the second film 182 pressed by the blades 132, and, further, they are heated. As a result, the elongate bodies 52 of the drug crystals provided on the wing outer portions 34a are broken, whereby the fixed-side elongate bodies 53 and the top-side elongate bodies 54 are formed (see FIG. 26). Note that it is not necessary that all the elongate bodies 52 should be broken.

In addition, since the portions of the outer surface of the balloon 30 which overlap with each other at the overlapping portions 35 are not exposed to the exterior, pressing forces act thereon indirectly from the blades 132. Therefore, the forces acting on the elongate bodies 52 provided on the portions of the outer surface of the balloon 30 which overlap with each other at the overlapping portions 35 can be easily controlled such as not to become excessively strong. For this reason, it is possible to exert desirable forces for forming the fixed-side elongate bodies 53 and the top-side elongate bodies 54 by breaking the elongate bodies 52 provided on the portions of the outer surface of the balloon 30 which overlap with each other at the overlapping portions 35. Accordingly, the desirable fixed-side elongate bodies 53 and the top-side elongate bodies 54 are formed on the portions of the outer surface of the balloon 30 which overlap with each other at the overlapping portions 35. In addition, in those regions of the wing inner portion 34b and the intermediate portion 34c facing each other which face the root-side space portion 36, namely, in the regions in which the wing inner portion 34b and the intermediate portion 34c are not in close contact with each other, the elongate bodies 52 are not liable (likely) to receive a pressing force. In the regions in which the wing inner portion 34b and the intermediate portion 34c are not in close contact with each other, therefore, the elongate bodies 52 are hardly broken, so that the fixed-side elongate bodies 53 and the top-side elongate bodies 54 are hardly formed. On the other hand, in those regions of the wing inner portions 34b and the intermediate portions 34c facing each other which do not face the root-side space portions 36, namely, in the regions in which the wing inner portion 34b and the intermediate portion 34c are in close contact with each other, the elongate bodies 52 are liable (likely) to receive a pressing force. In the regions in which the wing inner portion 34b and the intermediate portion 34c are in close contact with each other, therefore, the elongate bodies 52 are liable to be broken, so that the fixed-side elongate bodies 53 and the top-side elongate bodies 54 are liable to be formed.

A method of using the balloon catheter according to the second embodiment will be described below by taking as an example a case of treating a stenosed part in a blood vessel. The steps ranging from insertion of the balloon 30 into the blood vessel and inflation of the balloon 30 at the stenosed part 300 are the same as in the first embodiments.

When the folded balloon 30 is inflated, the stenosed part 300 is pushed wide open (i.e., open) by the balloon 30. In this instance, the coating layer 40 containing the drug crystals provided on the outer surface of the balloon 30 makes contact with the stenosed part 300. Since the elongate bodies 52 which are drug crystals contained in the coating layer 40 include the fixed-side elongate bodies 53 and the top-side elongate bodies 54, the density of the crystals on the outer surface of the balloon 30 is higher as compared to that in the case where the elongate bodies 52 do not include the fixed-side elongate bodies 53 and the top-side elongate bodies 54. In addition, since end portions of the fixed-side elongate bodies 53 and the top-side elongate bodies 54 are sharp (i.e., having an edge or point), they easily pierce the stenosed part 300, and, further, since the top-side elongate bodies 54 are independent from the fixed-side elongate bodies 53, they are easily moved to the stenosed part 300. Therefore, the surface area of the crystals making contact with the stenosed part 300 is enlarged, and the drug is effectively delivered from the outer surface of the balloon 30 to the stenosed part 300. Consequently, restenosis of the stenosed part 300 is effectively restrained.

When the balloon 30 is inflated to press the coating layer 40 against the living body tissue, the drug is delivered to the living body while the base material 41 which is the water-soluble low molecular weight compound contained in the coating layer 40 is being dissolved gradually or rapidly. Since the elongate bodies 52a, 52b and 52c which are crystals of the drug are different in the position of their base portions 55 in relation to the base material 41, they differ in deliverability to the living body tissue attendant on the gradual or rapid dissolution of the base material 41. In addition, the inflation of the balloon 30 causes the base material 41 to be cracked and be dissolved more easily, so that the elongate bodies 52 as the drug crystals are released from the base material 41 more easily. For this reason, it is possible, by regulating the positions of the base portions 55 of the elongate bodies 52 and thereby providing the elongate bodies 52a, 52b and 52c different in solubility, to arbitrarily set the deliverability of the drug.

Thereafter, the inflation fluid is sucked and discharged through the proximal opening portion 27 of the hub 26, to deflate the balloon 30 and put it into a folded state. Thereafter, the guide wire 200 and the balloon catheter 10 are withdrawn out of the blood vessel through the introducer, whereby the procedure is completed.

As has been described above, the balloon catheter 10 according to the second embodiment is a catheter provided on the outer surface of the balloon 30 with a plurality of elongate bodies 52 which are independent crystals of a water-insoluble drug extending in an elongate form, wherein the elongate bodies 52 include the fixed-side elongate bodies 53 which are fixed to the outer surface side of the balloon 30, and the top-side elongate bodies 54 which are independent from the fixed-side elongate bodies 53 and are not fixed to the outer surface side of the balloon 30 but are held between the plurality of fixed-side elongate bodies 53. The amount of the fixed-side elongate bodies 53 is greater than the amount of the top-side elongate bodies 54. In the balloon catheter 10 configured in this way, the elongate bodies 52 which are the crystals of the water-insoluble drug are separated into the fixed-side elongate bodies 53 and the top-side elongate bodies 54, and the top-side elongate bodies 54 are held between the fixed-side elongate bodies 53, which helps ensure that the density of the crystals of the drug on the outer surface of the balloon 30 is enhanced, and the surface area of the crystals making contact with the living body tissue is enlarged. In addition, the end portions of the fixed-side elongate bodies 53 and the top-side elongate bodies 54 easily pierce the living body tissue, and, further, the top-side elongate bodies 54 are easily moved to the living body tissue since they are independent from the fixed-side elongate bodies 53. For this reason, releasing property of the drug from the outer surface of the balloon 30 and transferability of the drug to the living body tissue can be enhanced, and the drug can be effectively delivered to the living body tissue.

In addition, the balloon 30 has the overlapping portions 35 where portions of the outer surface of the balloon 30 overlap with each other when the balloon 30 is folded in the deflated state, and the fixed-side elongate bodies 53 and the top-side elongate bodies 54 are provided on the portions of the outer surface of the balloon 30 which overlap with each other at the overlapping portions 35. For this reason, the fixed-side elongate bodies 53 and the top-side elongate bodies 54 are not exposed to the exterior in the deflated state, and, therefore, the fixed-side elongate bodies 53 and the top-side elongate bodies 54 can be protected until the balloon 30 reaches the target position. Accordingly, the drug can be restrained from falling off the outer surface of the balloon 30 or flowing away into blood stream or the like during delivery, and the drug can be delivered to the living body tissue more effectively.

In addition, the top-side elongate bodies 54 may have end portions in contact with the outer surface of the balloon 30 side. As a result of this, the top-side elongate bodies 54 are favorably held on, without falling off, the outer surface of the balloon 30, so that the top-side elongate bodies 54 can be carried (i.e., moved) favorably.

In addition, the water-insoluble drug may be rapamycin, paclitaxel, docetaxel, or everolimus. As a result of this, restenosis of the stenosed part in a blood vessel can be favorably restrained by the fixed-side elongate bodies 53 and the top-side elongate bodies 54.

In addition, the method of manufacturing the balloon catheter 10 according to the second embodiment is a method of manufacturing a balloon catheter 10 having on the outer surface of the balloon 30 a plurality of elongate bodies 52 which are crystals of a water-insoluble drug extending while having independent long axes, the method including the steps of: forming the elongate bodies 52 on the outer surface of the balloon 30; forming the balloon 30 with wing portions 32 projecting in radial directions; and folding the wing portions 32 formed in the balloon 30 along the circumferential direction, wherein in at least one of the step of forming the wing portions 32 and the step of folding the wing portions 32, the elongate bodies 52 are broken on the distal side by forces exerted for deforming the balloon 30, to separate the elongate bodies 52 into fixed-side elongate bodies 53 which are fixed to the outer surface side of the balloon 30 and top-side elongate bodies 54 which are independent from the fixed-side elongate bodies 53, and to hold the top-side elongate bodies 54 between a plurality of fixed-side elongate bodies 53. According to the method of manufacturing the balloon catheter 10 configured as above, it can be relatively easy, by utilizing the forces acting on the balloon 30 in the step of forming the balloon 30 with the wing portions 32 or in the step of folding the wing portions 32, to form the fixed-side elongate bodies 53 and the top-side elongate bodies 54 relatively efficiently, to push the separated top-side elongate bodies 54 in between a plurality of fixed-side elongate bodies 53, and thereby to put the top-side elongate bodies 54 into a state of being held between the plurality of fixed-side elongate bodies 53.

In addition, in the step of folding the wing portions 32, it is possible to form the overlapping portions 35 where portions of the outer surface of the balloon 30 face each other and overlap with each other, to break the elongate bodies 52 provided on the portions of the outer surface which face each other at the overlapping portions 35, and thereby to form the fixed-side elongate bodies 53 and the top-side elongate bodies 54, which helps ensure that since the forces exerted on the balloon 30 for folding the wing portions 32 act on the overlapping portions 35 in an indirect manner, it is possible to control the forces acting on the elongate bodies 52, and it is easy to exert desirable forces for separating the elongate bodies 52 into the fixed-side elongate bodies 53 and the top-side elongate bodies 54. In other words, in regard of the outer surface of the balloon 30 located at the overlapping portions 35, not only a state in which external forces act on the outer surface of the balloon 30, but also a state can in which external forces hardly act on the outer surface of the balloon 30. Therefore, the fixed-side elongate bodies 53 and the top-side elongate bodies 54 can be formed relatively efficiently.

In addition, the present disclosure also includes a treatment method (therapy) method of delivering a drug to a lesion affected area in a body lumen by use of the aforementioned balloon catheter 10. The treatment method includes the steps of: inserting the balloon 30 into the body lumen to deliver the balloon 30 to the lesion affected area; inflating the balloon 30 to press the fixed-side elongate bodies 53 and the top-side elongate bodies 54 against the living body tissue; and deflating the balloon 30 and withdrawing the balloon 30 out of the body lumen. According to the treatment method configured in this way, since the balloon 30 high in density of the crystals on the outer surface of the balloon 30 due to the top-side elongate bodies 54 being held between the fixed-side elongate bodies 53 is pressed against the living body tissue, the surface area of the crystals making contact with the living body tissue is enlarged. In addition, of the fixed-side elongate bodies 53 and the top-side elongate bodies 54, the broken and separated end portions are liable to become sharp and to pierce the living body tissue, and, further, the top-side elongate bodies 54 are easily moved to the living body tissue because they are independent from the fixed-side elongate body 53. For this reason, releasing property of the drug from the outer surface of the balloon 30 and transferability of the drug to the living body tissue can be enhanced, and the drug can be delivered to the living body tissue effectively.

Note that while the elongate bodies 52 formed on the outer surface of the balloon 30 are separated into the fixed-side elongate bodies 53 and the top-side elongate bodies 54 in the process of folding the balloon 30 in the second embodiment, the elongate bodies 52 may be separated by pressing by the blades 122 in the process of pleating (see FIG. 15).

Figure 29:
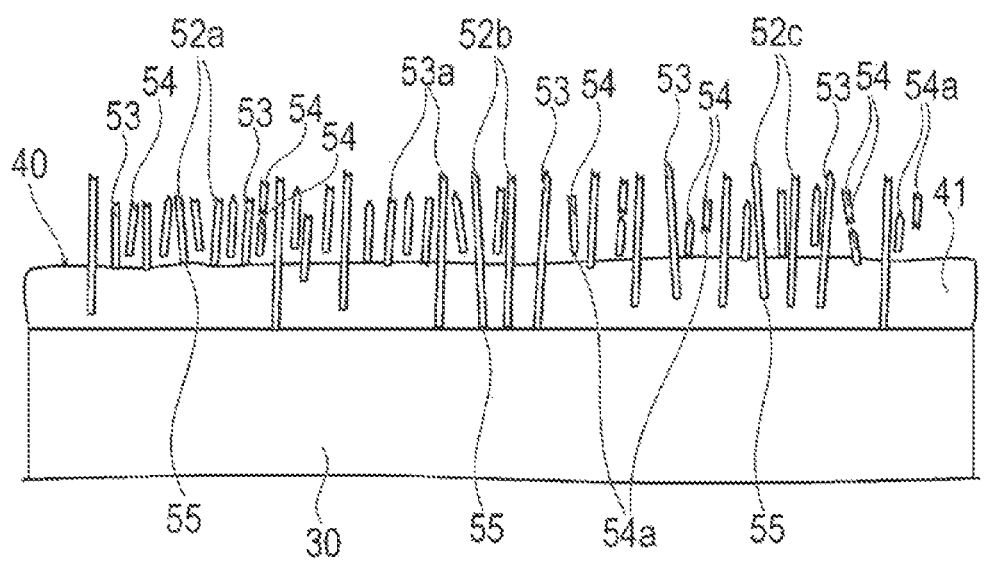
FIG. 29 is a schematic view depicting elongate bodies and a base material according to the second embodiment in the case where the base material is film-shaped and amorphous.
Figure 30:
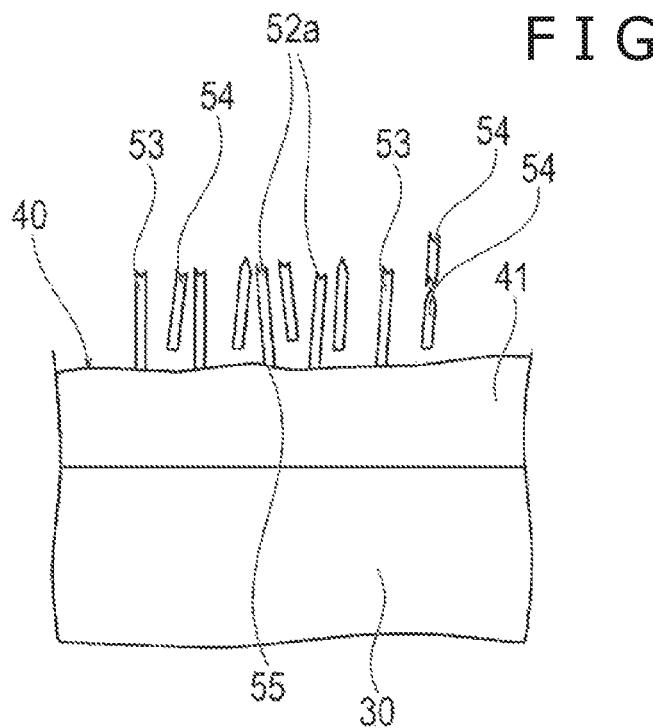
FIG. 30 is a schematic view of first elongate bodies and the base material on the outer surface of the balloon according to the second embodiment.
Figure 31:
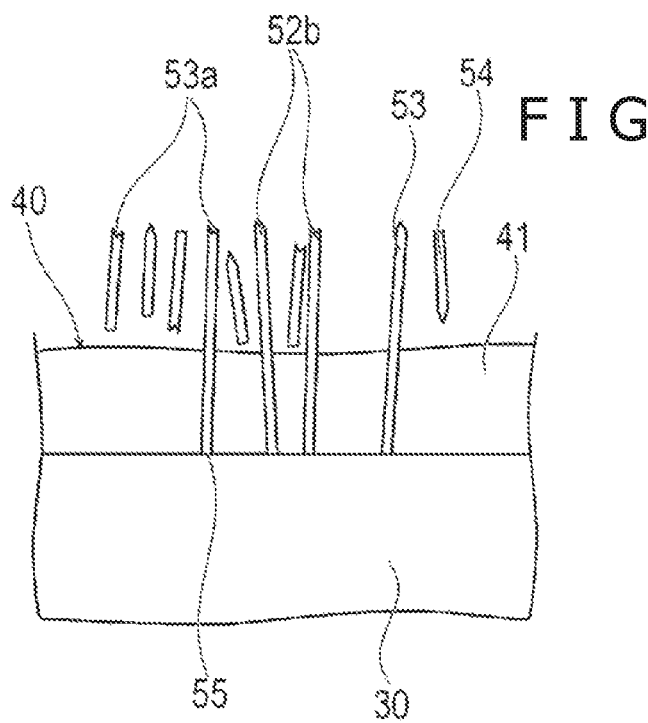
FIG. 31 is a schematic view of second elongate bodies and the base material on the outer surface of the balloon according to the second embodiment.
Figure 32:
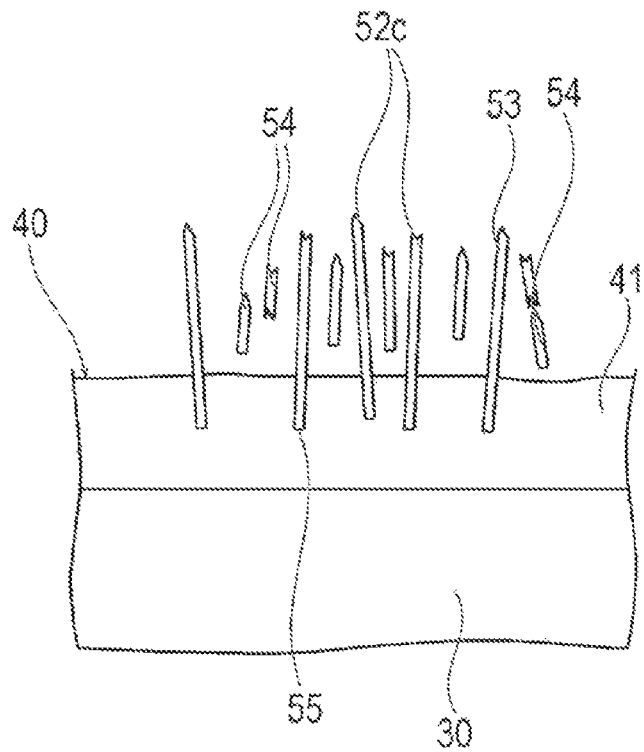
FIG. 32 is a schematic view of third elongate bodies and the base material on the outer surface of the balloon according to the second embodiment.

As aforementioned, the base material 41 is present as an amorphous phase, crystal particles or a mixture of them. While the base material 41 in FIG. 27 is in a state of crystal particles and/or a particulate amorphous phase, the base material 41 may be in a film-shaped amorphous state, as depicted in FIG. 29. As depicted in FIG. 30, the first elongate bodies 52a extend from the outer surface of the base material 41 toward an outside of the surface. As depicted in FIG. 31, the second elongate bodies 52b extend from the outer surface of the balloon 30 to the exterior of the base material 41 by penetrating the base material 41. As depicted in FIG. 32, the third elongate bodies 52c extend from the inside of the base material 41 to the outside of the base material 41.

Figure 33:
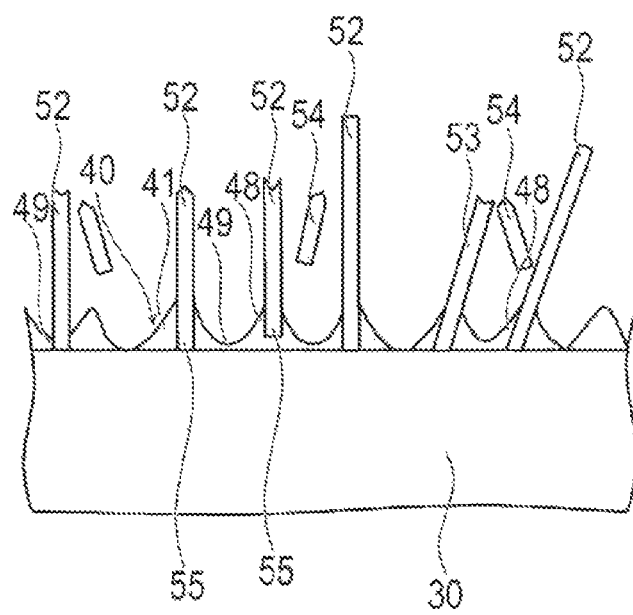
FIG. 33 is a schematic view of the elongate bodies and the base material on the outer surface of the balloon according to the second embodiment.

In addition, as depicted in FIG. 33, the base material 41 which is an additive layer may have projections and recesses (i.e., ruggedness). The height of the projections can be, for example, 0.1 µm to 5 µm. The elongate bodies 52 which are crystals are projecting from projecting portions 48 that constitute the projections of the base material 41. In other words, the elongate bodies 52 which are crystals are supported by the projecting portions 48 of the base material 41. Note that the base material 41 may have the projecting portions 48 from which the elongate bodies 52 are not projecting. The elongate bodies 52 which are crystals may project from recessed portions 49 that constitute the projections of the base material 41. The base material 41 may have both the projecting portions 48 which support the elongate bodies 52 and the projecting portions 48 which do not support the elongate bodies 52. The base material 41 may have both the recessed portions 49 which support the elongate bodies 52 and the recessed portions 49 which do not support the elongate bodies 52. In addition, the base material 41 may have both the projecting portions 48 which support the elongate bodies 52 and the recessed portions 49 which support the elongate bodies 52. The elongate bodies 52 may project obliquely from the base material 41 such as to be inclined relative to the outer surface of the balloon 30. The base material 41 may have both the elongate bodies 52 which are substantially perpendicular to the outer surface of the balloon 30 and the elongate bodies 52 which are inclined relative to the outer surface of the balloon 30. The base portions 55 of the elongate bodies 52 may be in direct contact with the outer surface of the balloon 30. Alternatively, the base portions 55 of the elongate bodies 52 may be located in the inside of the base material 41, without making contact with the outer surface of the balloon 30. The base material 41 may have both the elongate bodies 52 which are in direct contact with the outer surface of the balloon 30 and the elongate bodies 52 which are not in contact with the outer surface of the balloon 30.

Figure 34:
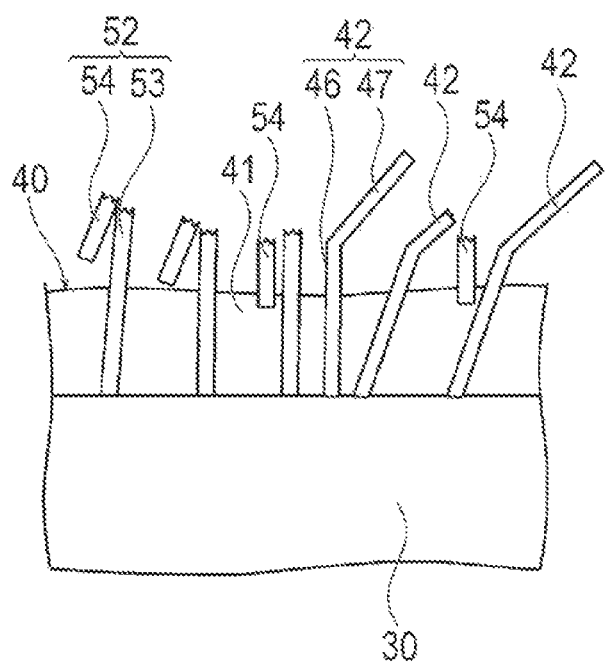
FIG. 34 is a schematic view depicting fixed-side elongate bodies, top-side elongate bodies and the base material on the outer surface of the balloon.

In addition, as depicted in FIG. 34, at least part of a distal portion, a proximal portion, and a portion between the distal portion and the proximal portion of the top-side elongate body 54 may be in contact with the base material 41. Part of the top-side elongate body 54 may be embedded in the base material 41. The presence of the base material 41 helps ensure that the fixed-side elongate bodies 53 and the top-side elongate bodies 54 are restrained, through an interaction with the base material 41, from falling off the balloon 30 during carrying of the balloon 30. The fixed-side elongate bodies 53 and the top-side elongate bodies 54 become liable (likely) to be released when the balloon 30 is inflated and the base material 41 is dissolved upon contact with water (blood). The fixed-side elongate bodies 53 and the top-side elongate bodies 54 which are different in form are different in releasing property, which is preferable from the viewpoint of acting on a living body. The fixed-side elongate bodies 53 may be formed through breaking of crystals, or may be formed without breaking of crystals. Both the fixed-side elongate bodies 53 which are formed through breaking of crystals and the fixed-side elongate bodies 53 which are formed without breaking of crystals may be fixed to the base material 41. The fixed-side elongate bodies 53 may be present in the state of standing from the base material 41 or may be present in the state of lying flat along the base material 41. The base material 41 may have both the fixed-side elongate bodies 53 which are standing from the base material 41 and the fixed-side elongate bodies 53 which are lying flat along the base material 41. In addition, the elongate bodies 42 in the first embodiment and the elongate bodies 52 in the second embodiment may coexist.

The length of the crystals fixed to the base material 41, before breaking of the crystals, is, 5 µm to 20 µm, for example. The length of the broken crystals is, for example, 3 µm to 20 µm. The length of the fixed-side elongate bodies 53 formed through the breaking is, for example, 5 µm to 20 µm. The length of the top-side elongate bodies 54 is, for example, 3 µm to 10 µm.

Note that the present disclosure is not limited to the aforementioned embodiment, and various modifications can be made by those skilled in the art within the technical thought of the present disclosure. For instance, while the balloon catheter 10 according to the above embodiment is of the rapid exchange type, the balloon catheter may be of the over-the-wire type.

The detailed description above describes a balloon catheter provided with a crystalline drug on a surface of a balloon and a method of manufacturing a balloon catheter, and a treatment method in which the balloon catheter is used. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A balloon catheter, the balloon catheter comprising:
a balloon having a plurality of elongate bodies on an outer surface of the balloon, the plurality of elongate bodies being crystals of a water-insoluble drug having independent long axes;
the plurality of elongate bodies including fixed-side elongate bodies that are fixed to an outer surface side of the balloon and top-side elongate bodies that are bent or broken from the fixed-side elongate bodies, the top-side elongate bodies being continuous with or independent of the fixed-side elongate bodies, the outer surface side of the balloon includes an outer surface of a coating layer formed on the outer surface of the balloon, and an inside of the coating layer formed on the outer surface of the balloon, and wherein the plurality of elongate bodies include first elongate bodies extending from the outer surface of the coating layer, second elongate bodies extending from the outer surface of the balloon, and third elongate bodies extending from the inside of the coating layer;
the balloon having an overlapping portion where portions of the outer surface of the balloon overlap with each other when the balloon is folded in a deflated state;
the fixed-side elongate bodies and the top-side elongate bodies are provided on portions of the outer surface of the balloon that overlap with each other at the overlapping portion;
the plurality of elongate bodies in the overlapping portion include the fixed-side elongate bodies that are fixed to the outer surface side of the balloon and the top-side elongate bodies that are bent or broken from the fixed-side elongate bodies the top-side elongate bodies that are bent from the fixed-side elongate bodies each have a longitudinal axis that is different than a longitudinal axis of the respective fixed-side elongate bodies; and wherein the plurality of elongate bodies includes elongate bodies having an angle of the longitudinal axes of the top-side elongate bodies relative to the longitudinal axes of the fixed-side elongate bodies between 30 degrees and 150 degrees.

2. The balloon catheter according to claim 1, wherein the water-insoluble drug is rapamycin, paclitaxel, docetaxel, or everolimus.

3. The balloon catheter according to claim 1, wherein the coating layer formed on the outer surface of the balloon is a drug-containing coating layer, and wherein the balloon of the balloon catheter includes a hollow cylindrical straight portion and tapered portions on both sides of the hollow cylindrical straight portion, and the drug-containing coating layer is formed on at least an entirety of the hollow cylindrical straight portion of the balloon.

4. The balloon catheter according to claim 1, wherein the plurality of elongate bodies in the overlapping portion including the fixed-side elongate bodies that are fixed to the outer surface side of the balloon and the top-side elongate bodies that are bent from the fixed-side elongate bodies are not exposed to an exterior in the deflated state of the balloon.

5. A method of manufacturing the balloon catheter according to claim 1, the method comprising:
forming the plurality of elongate bodies on the outer surface of the balloon;
forming the balloon to comprise a wing portion projecting in a radial direction;
folding along a circumferential direction of the wing portion formed in the balloon and forming the overlapping portion where the portions of the outer surface of the balloon face each other and overlap with each other, and the plurality of elongate bodies provided at facing outer surface portions of the overlapping portion are bent or broken to form the fixed-side elongate bodies and the top-side elongate bodies; and
wherein in at least one of the forming the balloon to comprise the wing portion or the folding along the circumferential direction of the wing portion, the plurality of elongate bodies are bent or broken by a force exerted for deforming the balloon, forming the fixed-side elongate bodies that are fixed to the outer surface side of the balloon and the top-side elongate bodies that are bent from the fixed-side elongate bodies and are continuous with the fixed-side elongate bodies, or top-side elongate bodies that are independent of the fixed-side elongate bodies.

6. The method of manufacturing the balloon catheter according to claim 5, further comprising:
folding the balloon along a circumferential direction of the wing portion in the deflated state.

7. The method of manufacturing the balloon catheter according to claim 5, further comprising:
forming the fixed-side elongate bodies and the top-side elongate bodies on the portions of the outer surface of the balloon that overlap with each other at the overlapping portion.

8. The method of manufacturing the balloon catheter according to claim 5, further comprising:
arranging a bent portion between each of the fixed-side elongate bodies and the top-side elongate bodies.

9. The method of manufacturing the balloon catheter according to claim 5, wherein the water-insoluble drug is rapamycin, paclitaxel, docetaxel, or everolimus.

10. A treatment method of delivering a drug to a lesion affected area in a body lumen by use of the balloon catheter of claim 1, the treatment method comprising:
inserting the balloon into the body lumen to deliver the balloon to the lesion affected area; and
inflating the balloon to press the fixed-side elongate bodies and the top-side elongate bodies against living body tissue.

11. The treatment method according to claim 10, further comprising:
deflating the balloon and withdrawing the balloon out of the body lumen.

12. The treatment method according to claim 10, wherein the top-side elongate bodies are continuous from the fixed-side elongate bodies, with a bent portion arranged between each of the fixed-side elongate bodies and the top-side elongate bodies.

13. The treatment method according to claim 10, wherein the water-insoluble drug is rapamycin, paclitaxel, docetaxel, or everolimus.

14. A balloon catheter, the balloon catheter comprising:
a balloon having a plurality of elongate bodies on an outer surface of the balloon, the plurality of elongate bodies being crystals of a water-insoluble drug having independent long axes;
the plurality of elongate bodies including fixed-side elongate bodies that are fixed to an outer surface side of the balloon and top-side elongate bodies that are bent or broken from the fixed-side elongate bodies, the top-side elongate bodies being continuous with the fixed-side elongate bodies or independent of the fixed-side elongate bodies;
wherein the top-side elongate bodies that are bent from the fixed-side elongate bodies each have a longitudinal axis that is different than a longitudinal axis of the respective fixed-side elongate body;
wherein the plurality of elongate bodies includes elongate bodies having an angle of the longitudinal axes of the top-side elongate bodies relative to the longitudinal axes of the fixed-side elongate bodies between 30 degrees and 150 degrees, the outer surface side of the balloon includes an outer surface of a drug-containing coating layer formed on the outer surface of the balloon, and an inside of the drug-containing coating layer formed on the outer surface of the balloon, and wherein the plurality of elongate bodies include first elongate bodies extending from the outer surface of the drug-containing coating layer, second elongate bodies extending from the outer surface of the balloon, and third elongate bodies extending from the inside of the drug-containing coating layer;
the balloon having an overlapping portion where portions of the outer surface of the balloon overlap with each other when the balloon is folded in a deflated state;
the fixed-side elongate bodies and the top-side elongate bodies are provided on portions of the outer surface of the balloon that overlap with each other at the overlapping portion; and
the plurality of elongate bodies in the overlapping portion being only the fixed-side elongate bodies that are fixed to the outer surface side of the balloon and the top-side elongate bodies that are bent or broken from the fixed-side elongate bodies, the top-side elongate bodies being continuous with or independent of the fixed-side elongate bodies, and wherein the elongate bodies in the overlapping portion are not exposed to an exterior in the deflated state of the balloon.

15. A balloon catheter, the balloon catheter comprising:
a balloon having a plurality of elongate bodies on an outer surface of the balloon, the outer surface of the balloon being smooth and non-porous, and the plurality of elongate bodies being crystals of a water-insoluble drug having independent long axes;
the plurality of elongate bodies including fixed-side elongate bodies that are fixed to an outer surface side of the balloon and top-side elongate bodies that are bent or broken from the fixed-side elongate bodies, the top-side elongate bodies being continuous with or independent of the fixed-side elongate bodies, the outer surface side of the balloon includes an outer surface of a coating layer formed on the outer surface of the balloon, and an inside of the coating layer formed on the outer surface of the balloon, and wherein the plurality of elongate bodies include first elongate bodies extending from the outer surface of the coating layer, second elongate bodies extending from the outer surface of the balloon, and third elongate bodies extending from the inside of the coating layer;
the balloon having an overlapping portion where portions of the outer surface of the balloon overlap with each other when the balloon is folded in a deflated state;
the fixed-side elongate bodies and the top-side elongate bodies are provided on portions of the outer surface of the balloon that overlap with each other at the overlapping portion; and
the plurality of elongate bodies in the overlapping portion include the fixed-side elongate bodies that are fixed to the outer surface side of the balloon and the top-side elongate bodies that are bent or broken from the fixed-side elongate bodies, the top-side elongate bodies being continuous with or independent of the fixed-side elongate bodies.

16. The balloon catheter according to claim 15, wherein the top-side elongate bodies are independent of the fixed-side elongate bodies, and are not fixed to the outer surface side of the balloon but are held between a plurality of the fixed-side elongate bodies.

17. The balloon catheter according to claim 15, wherein the top-side elongate bodies have end portions in contact with the outer surface side of the balloon.

18. The balloon catheter according to claim 15, wherein
the top-side elongate bodies are continuous with the fixed-side elongate bodies;
the top-side elongate bodies each have a longitudinal axis that is different than a longitudinal axis of the respective fixed-side elongate body: and
the plurality of elongate bodies include elongate bodies having an angle of the longitudinal axes of the top-side elongate bodies relative to the longitudinal axes of the fixed-side elongate bodies between 30 degrees and 150 degrees.

19. The balloon catheter according to claim 15, wherein the water-insoluble drug is rapamycin, paclitaxel, docetaxel, or everolimus.

20. The balloon catheter according to claim 15, wherein the plurality of elongate bodies include elongate bodies each having an angle of a longitudinal axis of the top-side elongate bodies relative to a longitudinal axis of the respective fixed-side elongate body between 30 degrees and 150 degrees.

* * * * *